US010837001B2

(12) United States Patent
Fong et al.

(10) Patent No.: US 10,837,001 B2
(45) Date of Patent: Nov. 17, 2020

(54) CARDIOMYOCYTE MATURATION PLATFORM

(71) Applicant: The Regents of the University of California, Oakland, CA (US)

(72) Inventors: Ashley H. Fong, Irvine, CA (US); Christopher C. W. Hughes, Irvine, CA (US)

(73) Assignee: The Regents of The University of California, Oakland, CA (US)

( * ) Notice: Subject to any disclaimer, the term of this patent is extended or adjusted under 35 U.S.C. 154(b) by 284 days.

(21) Appl. No.: 15/448,505

(22) Filed: Mar. 2, 2017

(65) Prior Publication Data
US 2017/0253858 A1 Sep. 7, 2017

Related U.S. Application Data

(60) Provisional application No. 62/303,326, filed on Mar. 3, 2016.

(51) Int. Cl.
*C12N 5/077* (2010.01)
*A61K 35/34* (2015.01)
*A61K 35/44* (2015.01)
*C12N 5/00* (2006.01)

(52) U.S. Cl.
CPC ............ *C12N 5/0657* (2013.01); *A61K 35/34* (2013.01); *A61K 35/44* (2013.01); *C12N 5/0012* (2013.01); *C12N 2501/727* (2013.01); *C12N 2502/28* (2013.01); *C12N 2502/45* (2013.01); *C12N 2503/02* (2013.01); *C12N 2503/04* (2013.01); *C12N 2506/45* (2013.01); *C12N 2513/00* (2013.01); *C12N 2533/90* (2013.01)

(58) Field of Classification Search
None
See application file for complete search history.

(56) References Cited

U.S. PATENT DOCUMENTS

2012/0064537 A1* 3/2012 Ross .................... C12N 5/0068
435/6.13
2013/0251687 A1* 9/2013 Christman ............ A61K 35/34
424/93.7

OTHER PUBLICATIONS

Van Laake, L.W., et al. Improvement of mouse cardiac function by hESC-derived cardiomyocytes correlates with vascularity but not graft size. Stem cell research. 2009;3:106-12.
Shiba, Y., et al.,Human ES-cell-derived cardiomyocytes electrically couple and suppress arrhythmias in injured hearts. Nature 489, 322, (2012).
Chong J.J. et al., Human embryonic-stem-cell-derived cardiomyocytes regenerate non-human primate hearts. Nature 510, 273, (2014.).
Ong, S.G et al., Microfluidic Single-Cell Analysis of Transplanted Human Induced Pluripotent Stem Cell-Derived Cardiomyocytes After Acute Myocardial Infarction. Circulation 132, 762, (2015).
Higuchi, T et al., Functional and Electrical Integration of Induced Pluripotent Stem Cell-Derived Cardiomyocytes in a Myocardial Infarction Rat Heart. Cell transplantation (2015).
Masumoto, H. et al., Human iPS cell-engineered cardiac tissue sheets with cardiomyocytes and vascular cells for cardiac regeneration. Scientific reports 4, 6716, (2014).
Yang, X. et al., Engineering adolescence: maturation of human pluripotent stem cell-derived cardiomyocytes. Circulation research 114, 511, (2014).
Lundy, S.D. et al., M.A.Structural and functional maturation of cardiomyocytes derived from human pluripotent stem cells. Stem cells and development 22, 1991, (2013).
Yang, X., Tri-iodo-l-thyronine promotes the maturation of human cardiomyocytes-derived from induced pluripotent stem cells. Journal of molecular and cellular cardiology 72, 296, (2014).
Zhang, D. et al., Tissue-engineered cardiac patch for advanced functional maturation of human ESC-derived cardiomyocytes. Biomaterials 34, 5813, (2013).
Otsuji, T.G. et al., Progressive maturation in contracting cardiomyocytes derived from human embryonic stem cells: Qualitative effects on electrophysiological responses to drugs. Stem cell research 4, 201, (2010).
Kim, C. et al., Non-cardiomyocytes influence the electrophysiological maturation of human embryonic stem cell-derived cardiomyocytes during differentiation. Stem cells and development 19, 783, (2010).
Tulloch, N.L. et al., Growth of engineered human myocardium with mechanical loading and vascular coculture. Circulation research 109, 47, (2011).
Kuppusamy, K.T et al., Let-7 family of micro RNA is required for maturation and adult-like metabolism in stem cell-derived cardiomyocytes. Proceedings of the National Academy of Sciences of the United States of America 112, E2785, (2015).

(Continued)

*Primary Examiner* — Blaine Lankford
(74) *Attorney, Agent, or Firm* — Accelerator AIX; Sean D. Senn

(57) ABSTRACT

Disclosed herein are methods of inducing and/or promoting cardiomyocyte maturation comprising: providing an immature cardiomyocyte; providing a three dimensional (3D) cardiac extracellular matrix (ECM) scaffold; and inducing and/or promoting cardiomyocyte cell maturation by seeding the immature cardiomyocyte in the 3D cardiac ECM scaffold and harvesting once the cardiomyocyte has reached maturity. Also disclosed herein are methods of treating a disease in a mammal comprising transplanting a mature cardiomyocyte into an ischemic heart, wherein the mature cardiomyocyte is generated comprising the steps of: providing an immature cardiomyocyte; providing a 3D cardiac ECM scaffold; and generating mature cardiomyocyte by seeding the immature cardiomyocyte in a 3D cardiac ECM scaffold or co-culturing the immature cardiomyocyte in the presence of endothelial cells or stromal cells; and harvesting once the cardiomyocyte has reached maturity.

6 Claims, 12 Drawing Sheets
Specification includes a Sequence Listing.

(56) References Cited

OTHER PUBLICATIONS

Lieu, D.K. et al., Mechanism-Based Facilitated Maturation of Human Pluripotent Stem Cell-Derived Cardiomyocytes. Circulation 6, 191, (2013).
Berkholtz, C.B. et al., Extracellular matrix functions in follicle maturation. Seminars in reproductive medicine 24, 262, (2006).
Solozobova, V. et al., Lessons from the embryonic neural stem cell niche for neural lineage differentiation of pluripotent stem cells. Stem cell reviews 8, 813, (2012).
Gao, Y. et al. The ECM-cell interaction of cartilage extracellular matrix on chondrocytes. BioMed research International 2014, 648459, (2014).
Zimmermann, D.R. et al., Extracellular matrix of the central nervous system: from neglect to challenge. Histochemistry and cell biology 130, 635, (2008).
Gieseck, R.L. et al., Maturation of induced pluripotent stem cell derived hepatocytes by 3D-culture. PloS one 9, e86372, (2014).
Otonkoski, T. et al., Unique basement membrane structure of human pancreatic islets: implications for beta-cell growth and differentiation. Diabetes, obesity & metabolism 10 Suppl 4, 119, (2008).
Dequach, J.A. et al., Simple and high yielding method for preparing tissue specific extracellular matrix coatings for cell culture. PloS one 5, e13039, (2010).
Duan, Y. et al., Hybrid gel composed of native heart matrix and collagen induces cardiac differentiation of human embryonic stem cells without supplemental growth factors. Journal of cardiovascular translational research 4, 605, (2011).
French, K.M., et al., A naturally derived cardiac extracellular matrix enhances cardiac progenitor cell behavior in vitro. Acta biomaterialia 8, 4357, (2012).
Singelyn, J.M. et al., Naturally derived myocardial matrix as an injectable scaffold for cardiac tissue engineering. Biomaterials 30, 5409, (2009).
Williams, C et al., Young developmental age cardiac extracellular matrix promotes the expansion of neonatal cardiomyocytes in vitro. Acta biomaterialia 10, 194, (2014).
Maddah, M. et al., A non-invasive platform for functional characterization of stem-cell-derived cardiomyocytes with applications in cardiotoxicity testing. Stem cell reports 4, 621, (2015).
Chen, T.W. et al., Ultrasensitive fluorescent proteins for imaging neuronal activity. Nature 499, 295, (2013).
Lian, X. et al., Directed cardiomyocyte differentiation from human pluripotent stem cells by modulating Wnt/beta-catenin signaling under fully defined conditions. Nature protocols 8, 162, (2013).
Theodossiou, T.A. et al., Second harmonic generation confocal microscopy of collagen type I from rat tendon cryosections. Biophysical journal 91, 4665, (2006).
Williams, R.N et al., Interpreting second-harmonic generation images of collagen I fibrils. Biophysical journal 88, 1377, (2005).
Crosignani, V. et al., A deep tissue fluorescence imaging system with enhanced SHG detection capabilities. Microscopy research and technique 77, 368, (2014).
Richard-Kortum, R. et al., Quantitative optical spectroscopy for tissue diagnosis. Annu Rev Phys Chem 47, 555, (1996).
Crosignani V. et al., Deep tissue fluorescence imaging and in vivo biological applications. Journal of Biomedical Optics 17, 116023, (2012).
Liu, J. et al., Functional sarcoplasmic reticulum for calcium handling of human embryonic stem cell-derived cardiomyocytes: insights for driven maturation. Stem cells 25, 3038, (2007).
Nunes, S.S. et al., Biowire: a platform for maturation of human pluripotent stem cell-derived cardiomyocytes. Nature methods 10, 781, (2013).
Zhang, M. et al., Universal cardiac induction of human pluripotent stem cells in two and three-dimensional formats: Implications for in vitro maturation. Stem cells 33, 1456, (2015).
Zimmermann, W.H et al., Tissue Engineering of a Differentiated Cardiac Muscle Construct. Circulation Research 90, 223, (2001).
Tallawi, M. et al., Effect of substrate mechanics on cardiomyocyte maturation and growth. Tissue engineering Part B, Reviews 21, 157, (2015).
Wendel, J.S. et al., Functional consequences of a tissue-engineered myocardial patch for cardiac repair in a rat infarct model. Tissue engineering Part A 20, 1325, (2014).
Bayomy, A.F. et al., Regeneration in heart disease—Is ECM the key? Life sciences 91, 823, (2012).
Ross, R.S. et al., Integrins and the Myocardium. Circulation Research 88, 1112, (2001).
Jacot, J.G. et al., Substrate stiffness affects the functional maturation of neonatal rat ventricular myocytes. Biophysical journal 95, 3479, (2008).
Rog-Zielinska, E.A. et al., Glucocorticoids promote structural and functional maturation of foetal cardiomyocytes: a role for PGC-1alpha. Cell death and differentiation 22, 1106, (2015).
Kong, H. et al., Caffeine induces Ca2+ release by reducing the threshold for luminal Ca2+ activation of the ryanodine receptor. The Biochemical journal 414, 441, (2008).
Jaramillo, M. et al., Endothelial cell co-culture mediates maturation of human embryonic stem cell to pancreatic insulin producing cells in a directed differentiation approach. Journal of visualized experiments: JoVE (2012).
Lee, D.S. et al., Defined MicroRNAs Induce Aspects of Maturation in Mouse and Human Embryonic-Stem-Cell-Derived Cardiomyocytes. Cell reports; 12:1960-7 (2015).
Hsiefi, P.C. et al., Endothelial-cardiomyocyte interactions in cardiac development and repair. Annual review of physiology; 68:51-66 (2006).
Drawnel, F.M. et al., The role of the paracrine/autocrine mediator endothelin-1 in regulation of cardiac contractility and growth. British journal of pharmacology; 168:296-317 (2013).
Paradis, A. et al., Endothelin-1 promotes cardiomyocyte terminal differentiation in the developing heart via heightened DNA methylation. International journal of medical sciences; 11:373-80 (2014).
Zhou, X.L. et al., Role of Notch signaling in the mammalian heart. Brazilian journal of medical and biological research / Revista brasileira de pesquisas medicas e biologicas 1 Sociedade Brasileira de Biofisica, 47:1-10 (2014).
Melero-Martin, J.M. et al., In vivo vasculogenic potential of human blood-derived endothelial progenitor cells. Blood. 109: 4761-8 (2007).
Rich S. et al., Endothelin receptor blockers in cardiovascular disease. Circulation. 08: 2184-90 (2003).
Koyanagi, M. et al., Notch signaling contributes to the expression of cardiac markers in human circulating progenitor cells. Circulation research;101:1139-45 (2007).

\* cited by examiner

CARDIOMYOCYTE MATURATION PLATFORM

RELATED APPLICATION

This application claims the benefit of priority from U.S. Provisional Patent Application No. 62/303,326, filed on Mar. 3, 2016, the entire disclosure of which is incorporated by reference, including the figures.

STATEMENT REGARDING FEDERALLY SPONSORED RESEARCH

This work was supported by grants UH3 TR00048 and SIG 1S10OD016328 awarded by the National Institutes of Health; grant DGE-0549479 awarded by the National Science Foundation; and grant TG2-01152 awarded by the California Institute of Regenerative Medicine. The U.S. Government has certain rights in the invention.

FIELD OF THE INVENTION

The present disclosure is in the medical and biomedical field, specifically in the field of cardiovascular diseases.

BACKGROUND OF THE DISCLOSURE

Cardiovascular disease is the number one cause of death in the world. One common manifestation is myocardial infarction, an ischemic event in the heart that results in the death of cardiomyocytes. The loss of cardiomyocytes can impair heart function, and repair is limited due to the extremely low proliferation rate of endogenous cardiomyocytes. Moreover, damaged tissue undergoes fibrosis which increases the risk of arrhythmia and subsequent heart failure. There is no available drug treatment that can regenerate the lost myocardium, resulting in a critical need to find new treatment strategies.

Previous studies in this field have focused on the potential regenerative capacity of exogenous cardiomyocytes as a treatment method. These cardiomyocytes are usually derived from induced pluripotent stem cells (iPSCs) generated from the patient's own cells. A limitation to this approach is that pluripotent stem cell-derived cardiomyocytes generated through methods currently available are immature, displaying characteristics of fetal cardiomyocytes. These immature cells show disorganized sarcomere structures, weak force contraction, automaticity (spontaneous beating), improper calcium handling and electrophysiological signaling, low expression of critical cardiac proteins, and altered responses to drugs when compared to mature cardiomyocytes.

Thus there exists a need in the art for mature cardiomyocytes, that outperform immature cardiomyocytes for tissue replacement strategies and screening of novel pharmacologic compounds, by producing stronger force contraction, and show appropriate calcium handling and electrophysiology.

In addition, the loss of automaticity seen in mature cardiomyocytes (which require pacemaker cells to trigger beating) improves safety by eliminating potential arrhythmic events. The use of mature cardiomyocytes for drug screening has clear advantages over the use of immature cells for predicting efficacy and potential side effects. Thus, a need exists for the efficient generation of mature cardiomyocytes, particularly generation of mature cardiomyocytes from iPSC.

SUMMARY OF THE DISCLOSURE

In various embodiments, disclosed herein are methods of inducing and/or promoting cardiomyocyte maturation comprising: providing an immature cardiomyocyte; providing a three dimensional (3D) cardiac extracellular matrix (ECM) scaffold; and inducing and/or promoting cardiomyocyte maturation by seeding the immature cardiomyocyte in the 3D cardiac ECM scaffold. In one embodiment, the 3D cardiac ECM is generated from a heart tissue of an adult subject through SDS-mediated decellularization. In one embodiment, the induction and/or promotion of cardiomyocyte maturation occurs in vitro. In one embodiment, the induction and/or promotion of cardiomyocyte maturation occurs in vivo. In one embodiment, the method further comprises providing endothelial cells in the 3D cardiac ECM scaffold, and wherein the endothelial cells induce maturation of the immature cardiomyocyte. In one embodiment, the method further comprises co-culturing the endothelial cells and immature cardiomyocytes in a conditioned medium. In one embodiment, the method further comprises providing stromal cells in the 3D cardiac ECM scaffold, and wherein the stromal cells induce maturation of the cardiomyocyte. In one embodiment, the cardiomyocytes maturation is demonstrated by an increase in expression of a maturation marker relative to the immature cardiomyocyte. In one embodiment, the maturation marker comprises one or more of the proteins: Junctin, SERCA2a, CaV1.2, NCX1, and/or Cx43. In one embodiment, the method further comprises harvesting the mature cardiomyocyte by separating it from the 3D cardiac ECM scaffold. In one embodiment, the 3D cardiac ECM is prepared comprising the steps: providing a heart tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D cardiac ECM scaffold by mixing the digested ECM. In one embodiment, the method further comprises mixing the digested ECM with fibrinogen. In one embodiment, the mature cardiomyocytes in combination with a carrier, diluent, and/or adjuvant are suitable for use in drug screening. In one embodiment, the mature cardiomyocytes in combination with a carrier, diluent, and/or adjuvant are suitable for use in tissue engineering therapy.

In various embodiments, disclosed herein are methods of treating a disease in a mammal comprising transplanting a mature cardiomyocyte into an ischemic heart, wherein the mature cardiomyocyte is generated comprising the steps of: providing an immature cardiomyocyte; providing a three dimensional (3D) cardiac extracellular matrix (ECM) scaffold; and generating mature cardiomyocytes by seeding the immature cardiomyocyte in the 3D cardiac ECM scaffold and harvesting once the cardiomyocyte has reached maturity. In one embodiment, the 3D cardiac ECM is generated from a heart tissue of an adult mammal through SDS-mediated decellularization. In one embodiment, the generation of the mature cardiomyocyte occurs in vitro. In one embodiment, the generation of the mature cardiomyocyte occurs in vivo. In one embodiment, the method further comprises providing endothelial cells in the 3D cardiac ECM scaffold. In one embodiment, the method further comprises providing stromal cells in the 3D cardiac ECM scaffold. In one embodiment, cardiomyocytes maturation is demonstrated by increase in expression of a maturation marker relative to a fetal cardiomyocyte cell. In one embodiment, the maturation marker comprises one or more of the proteins: Junctin, SERCA2a, CaV1.2, NCX1, and/or Cx43. In one embodiment, the 3D cardiac ECM is prepared comprising the steps: providing a heart tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D cardiac ECM scaffold by mixing the digested ECM with fibrinogen. In one embodiment, the subject is an adult subject.

In various embodiments, disclosed herein are compositions comprising a 3D extracellular matrix (ECM) scaffold and one or more cardiomyocytes. In one embodiment, the 3D ECM scaffold is prepared comprising the steps: providing a tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D ECM scaffold by mixing the digested ECM with fibrinogen. In one embodiment, the subject is an adult subject.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
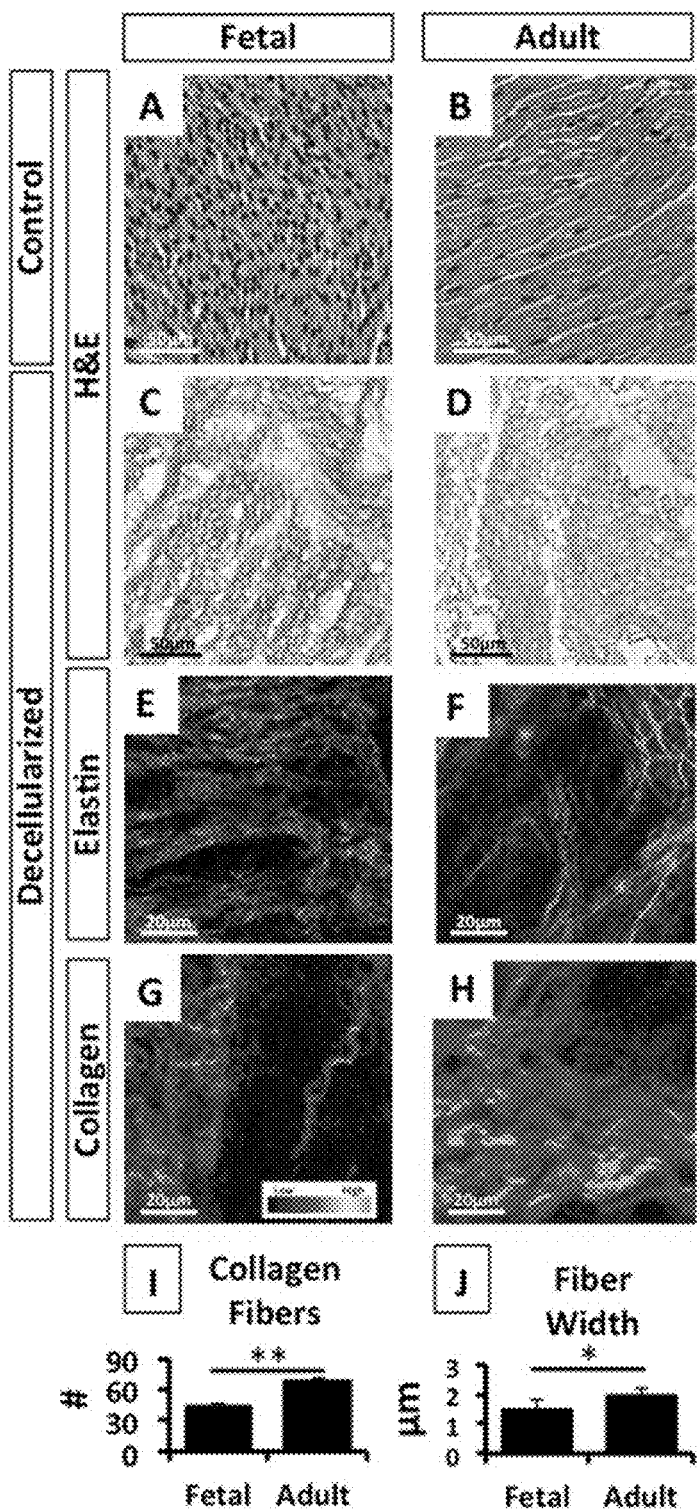
FIG. 1 illustrates, in accordance with embodiments herewith, the characterization of cardiac ECM from decellularized bovine fetal and adult heart tissue. Decellularized adult bovine cardiac tissue has a more prominent fibrillar structure than fetal cardiac tissue. Panels A, C, E, and G refer to fetal heart tissue, while panels B, D, F, and H refer to adult heart tissue. Panels A and B illustrates an embodiment of control tissue while panels C through H illustrates different embodiments of decellularized tissue. Panels E and F illustrates elastin fibers visualized by autofluorescence at 860 nm. Panels G and H illustrates collagen fibers visualized by second harmonic generation at 740 nm. Panel I is a quantification of the number of collagen fibers comparing fetal and adult decellularized cardiac tissue. Finally, panel J illustrates collagen fiber width comparing fetal and adult decellularized cardiac tissue. Results are expressed as mean±standard error. (n=3; *$p<0.05$ **$p<0.01$, Student's t-test).

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "immature" cell or "fetal" cell, as used herein, refers to cells that are in various stages of differentiation from undifferentiated stem cells to progenitor cells and other cells such as various precursor cells and neutrophils, which are partially differentiated, and excludes cells that are fully differentiated.

The term "cardiac microenvironment," as used herein, refers to the cellular environment in which the heart (cardiac) cells exists, comprising, but not limited to, surrounding blood vessels, cardiomyocytes, pacemaker cells, stromal cells, and the extracellular matrix (ECM). In some embodiments, the natural cardiac micro-environment is mimicked in vitro by exposing immature cardiomyocytes to a three dimensional scaffold of cardiac extracellular matrix.

The terms "seed," "seeding," and "seeded," as used herein, refers to the process of loading or inoculating a scaffold or a cell culture medium with one or more cells or interest, such as tissue regenerating cells. In one embodiment, seeding may be performed by injection of immature cardiomyocytes onto and/or into the scaffold. In another embodiment, seeding may be performed by co-culturing immature cardiomyocytes and endothelial cells and/or stromal cells in a cell culture media. As readily apparent to one of skill in the art, there are many techniques available for seeding, and the present disclosure is not limited to the specific seeding techniques disclosed herein.

In various embodiments, disclosed herein are methods of making and using mature cardiomyocytes for the diagnosis, prognosis and/or treatment of cardiovascular diseases. The inventors have combined multiple parameters of the cardiac microenvironment in order to induce and promote CM maturation. These parameters include, but are not limited to, utilizing a three dimensional cardiac ECM scaffold and vasculature as the microenvironment that induces CM maturation. The mature CM generated from this method platform can be used for studying pathological and developmental stages within the heart, drug screening, and cardiac regeneration through cellular and tissue engineering therapies to treat diseases.

In one embodiment, provided herein is a method of inducing and/or promoting cardiomyocyte cell maturation comprising: providing an immature cardiomyocyte; providing a three dimensional (3D) cardiac extracellular matrix (ECM) scaffold; and inducing and/or promoting cardiomyocyte maturation by seeding the immature cardiomyocytes in the 3D cardiac ECM scaffold and harvesting once the cardiomyocyte has reached maturity. In one embodiment, the 3D cardiac ECM is generated from a heart tissue of an adult subject through SDS-mediated decellularization. In one embodiment, the induction and/or promotion of cardiomyocyte maturation occurs in vitro. In one embodiment, the induction and/or promotion of cardiomyocyte cell maturation occurs in-vivo. In one embodiment, the method further comprises providing endothelial cells in the 3D cardiac ECM scaffold. In one embodiment, the method further comprises providing stromal cells in the 3D cardiac ECM scaffold. In one embodiment, the cardiomyocyte maturation is demonstrated by increase in expression of a maturation marker relative to a fetal cardiomyocytes. In one embodiment, the maturation marker comprises one or more of the proteins: Junctin, SERCA2a, CaV1.2, NCX1, and/or Cx43. In one embodiment, the 3D cardiac ECM is prepared comprising the steps: providing a heart tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D cardiac ECM scaffold by mixing the digested ECM with fibrinogen. In one embodiment, the mature cardiomyocytes in combination with a carrier, diluent, and/or adjuvant are suitable for use in drug screening. In one embodiment, the mature cardiomyocytes in combination with a carrier, diluent, and/or adjuvant are suitable for use in tissue engineering therapy.

In one embodiment, provided herein is a method of treating a disease in a mammal comprising transplanting mature cardiomyocytes into an ischemic heart, wherein the mature cardiomyocytes are generated comprising the steps of: providing an immature cardiomyocyte; providing a three dimensional (3D) cardiac extracellular matrix (ECM) scaffold; and generating mature cardiomyocytes by seeding the immature cardiomyocyte in the 3D cardiac ECM scaffold and harvesting once the cardiomyocyte cell has reached maturity. In one embodiment, the 3D cardiac ECM is generated from a heart tissue of an adult mammal through SDS-mediated decellularization. In one embodiment, the generation of mature cardiomyocyte occurs in vitro. In one embodiment, the generation of mature cardiomyocyte cell occurs in-vivo. In one embodiment, the method further comprises providing endothelial cells in the 3D cardiac ECM scaffold. In one embodiment, the method further comprises providing stromal cells in the 3D cardiac ECM scaffold. In one embodiment, the cardiomyocytes maturation is demonstrated by increase in expression of a maturation marker relative to a fetal cardiomyocyte cell. In one embodiment, the maturation marker comprises one or more of the proteins: Junctin, SERCA2a, CaV1.2, NCX1, and/or Cx43. In one embodiment, the 3D cardiac ECM is prepared comprising the steps: providing a heart tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D cardiac ECM scaffold by mixing the digested ECM with fibrinogen.

In one embodiment, provided herein is a composition comprising a 3D extracellular matrix (ECM) scaffold and one or more cardiomyocytes. In one embodiment, the 3D ECM scaffold is prepared comprising the steps: providing a tissue of a subject; decellularizing the tissue by incubating it in a solution comprising SDS for 2-5 days and subsequent washing with water; preparing digested ECM by grating the decellularized tissue to a powder form followed by digestion with pepsin; and preparing the 3D ECM scaffold by mixing the digested ECM with fibrinogen.

In one embodiment, provided herein are methods of inducing and/or promoting cardiomyocyte cell maturation comprising: (a) providing an immature cardiomyocyte cell; (b) providing endothelial cells or stromal cells; and (c) inducing and/or promoting cardiomyocyte cell maturation by co-culturing the immature cardiomyocyte with the endothelial cells and/or stromal cells.

In one embodiment, provided herein are methods of using mature cardiomyocytes as a drug screening platform, wherein the mature cardiomyocyte cells are generated comprising the steps of: providing an immature cardiomyocyte cell; providing a 3D cardiac ECM scaffold or presence of EC or stromal cells; and generating mature cardiomyocyte cells by seeding the immature cardiomyocyte in the 3D cardiac ECM scaffold and harvesting once the cardiomyocyte has reached maturity.

Various embodiments of the present disclosure include methods of generating cardiomyocytes in vitro, by exposing fetal or immature cardiomyocytes to an environment similar to their natural cardiac micro-environments. In some embodiments, other cell types are present in the three dimensional scaffold of extracellular matrix. In some embodiments, the other cell types comprise endothelial cells or stromal cells. In some embodiments, the three dimensional scaffold is a single extracellular matrix protein, synthetic scaffolds, biodegradable scaffolds, or hydrogels. In some embodiments, the three dimensional scaffold is cardiac extracellular matrix. In one embodiment, the cardiac extracellular matrix is fetal cardiac extracellular matrix or adult cardiac extracellular matrix.

In one embodiment, cardiomyocyte maturation is promoted in an endothelial cell conditioned medium. In another embodiment, cardiomyocyte maturation is promoted when cardiomyocytes are co-cultured with endothelial cells. In some of these embodiments, cardiomyocyte maturation is demonstrated by increases in expression of the maturation markers, Junctin, SERCA2a, CaV1.2, NCX1, and/or Cx43.

In another embodiment of the present disclosure, presented herein are methods of treating cardiovascular disease in a mammal by transplanting mature cardiomyocytes into ischemic hearts, wherein the mature cardiomyocyte is generated in vitro, by exposing fetal cardiomyocytes to an environment similar to their natural cardiac micro-environment. In some embodiments, the natural cardiac micro-environment is mimicked in vitro by exposing fetal cardiomyocytes to a three dimensional scaffold of cardiac extracellular matrix. In one embodiment, other cell types are present in the three dimensional scaffold of extracellular matrix, such as endothelial cells or stromal cells. In some embodiments, the three dimensional scaffold is a single extracellular matrix protein, synthetic scaffolds, biodegradable scaffolds, or hydrogels. In some embodiments, the three dimensional scaffold is cardiac extracellular matrix. In one embodiment, the cardiac extracellular matrix is fetal cardiac extracellular matrix or adult cardiac extracellular matrix. In one embodiment, cardiomyocyte maturation is promoted in an endothelial cell conditioned medium. In another embodiment, cardiomyocyte maturation is promoted when cardiomyocytes are co-cultured with endothelial cells. In some of these embodiments, cardiomyocyte maturation is demonstrated by increases in expression of the maturation markers, Junctin, SERCA2a, CaV1.2, NCX1, and/or Cx43.

In one embodiment, disclosed herein is a method for prognosing a cardiovascular disease in a subject comprising: (a) Obtaining a cell sample from the subject's heart, (b) Assaying the sample to determine the amount of cardiomyocytes, (c) Comparing the amount of cardiomyocytes to that of a healthy subject, and (d) Prognosing the severity of cardiovascular disease based on the decrease in the amount of cardiomyocytes in the subject.

In one embodiment, disclosed herein is a method for diagnosing cardiovascular disease in a subject at risk of developing cardiovascular disease, or for diagnosing a risk of developing cardiovascular disease in a subject, comprising: (a) Obtaining a cell sample from the subject's heart, (b) Assaying the sample to determine the amount of cardiomyocytes, (c) Comparing the amount of cardiomyocytes to that of a healthy subject, and (d) Prognosing the severity of cardiovascular disease based on the decrease in the amount of cardiomyocytes in the subject. In one embodiment, provided herein is a method of screening for treatment of a disease in a subject, comprising: providing mature cardiomyocytes in the subject; and screening for the treating of the disease based on the amount of mature cardiomyocytes. In one embodiment, provided herein is a method of inducing and/or promoting cell maturation comprising providing a cell; and utilizing a 3D extracellular matrix. In one embodiment, the cells are cardiomyocyte cells. In one embodiment, provided herein is a composition comprising a 3D extracellular matrix scaffold and one or more cardiomyocyte cells.

The present disclosure provides compositions, which in one embodiment, may be a pharmaceutical composition. In one embodiment, the pharmaceutical composition further comprises a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrastemal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment, the route of administration may be a surgery for insertion of tissue engineering constructions, injected through a catheter.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21st edition, Williams & Wilkins Pa., USA) (2005).

Typical dosages of an effective composition can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

Embodiments of the present disclosure are further described in the following examples. The examples are merely illustrative and do not in any way limit the scope of the invention as claimed.

EXAMPLES

Example 1 iPSC Maintenance and Cardiac Differentiation

All experiments were performed with approval from UC Irvine's Human Stem Cell Research Oversight Committee and used the human WTC-11 GCaMP iPSC line. The WTC-11 iPSC line was derived from a healthy male volunteer with a normal electrocardiogram and no known family history of cardiac disease. The GCaMP iPSC line was generated using nuclease-mediated (TALEN) introduction of GCaMP6f, and the resulting cell line reports calcium fluxes through GFP fluorescence. The iPSC were maintained on Growth Factor Reduced Matrigel (Corning, Salt Lake City, Utah) and fed daily with mTeSR1 medium (StemCell Technologies, Vancouver, Canada). To induce cardiomyocyte differentiation, iPSC were seeded as single cells into 12 well plates coated with 1 mg Matrigel Growth Factor Reduced (BD #354230), in the presence of 10 nM Y-27632 (Ascent, Cambridge, Mass.). Cardiac induction was initiated 2-4 days later (designated as Day 0), when cells were 75-90% confluent, by the addition of glycogen synthase kinase 3 inhibitor (CHIR99021, 6 µM, Tocris Inc, Bristol, United Kingdom) in RPMI/B27 (without insulin, Life Technologies, Carlsbad, Calif.). Twenty-four hours later (Day 1) the medium was changed to fresh RPMI/B27 (without insulin). On Day 3, Wnt inhibitor (IWP2, 5 µM, Tocris) was added in RMPI/B27 (without insulin), and at Day 5 cells were fed fresh RMPI/B27 (without insulin). The cells were subsequently fed RMPI/B27 (with insulin) (Life Technologies) every 3 days starting at Day 7. Cells began to spontaneously beat by Day 12.

Example 2

Cardiac Tissue Decellularization and Extracellular Matrix Generation

Bovine adult and fetal hearts were purchased from Sierra Medical. Prior to decellularization the tissue (100-200 g) was processed by removing all excess fat, and stored at −80° C. for at least 16 hours. Next the tissue was cut into 3 mm$^3$ sized pieces and subjected to continuous stirring at 330 RPM during incubation in the following solutions at room temperature: ddH$_2$O for 30 min, 2×PBS for 15 min, sodium dodecyl sulfate (SDS) (1% for adult tissue and 0.5% for fetal tissue, Bio-Rad) for 72 hours, and 1% Triton for 90 min. This was followed by 7 washes in ddH$_2$O for 30 min each, and 18 hours in PBS with Antibiotic-Antimycotic (Life Technologies) at 4° C.

Decellularized tissues were lyophilized and then milled using a cheese grater (Amazon.com, Seattle, Wash.) to create a fine powder. The extracellular matrix powder was digested with 2 mg/ml pepsin (Sigma-Aldrich, St. Louis, Mo.) diluted in 0.01 M cell culture grade hydrochloric acid (HCl). Approximately 200 mg of cardiac extracellular matrix was added to 20 mg of pepsin and continuously stirred at 330 RPM at room temperature for 48-72 hours or until fully digested. The digested extracellular matrix was divided into 1 ml aliquots and stored at −80° C. until needed.

Example 3

Multiphoton Imaging and Fiber Analysis

Fibrillar collagen generates second-harmonic (SHG) signals when incident light interacts with its non-centrosymmetric structure, and SHG microscopy has been widely used to study collagen fibers in vivo and in vitro. In addition, elastin fibers are autofluorescent due to elastin's tricarboxilic, triamino pyridinium derivatives, and are therefore visualized using multiphoton microscopy.

Imaging was performed in the Laboratory for Fluorescence Dynamics (LFD) at UCI. A Ti:Sapphire laser (Mai Tai, Spectra Physics, Irvine, Calif.) was used for two-photon fluorescence excitation with a wavelength of 740 nm (SHG) and 860 nm (autofluorescence) with an incident power of 20 mW. The signal was collected using a water objective with a long working distance (LUMPlanFl 40×/0.80 W, Olympus, Tokyo, Japan). The SHG signal was obtained using a 320 nm-390 nm bandpass filter. The autofluorescent signal was collected using a 500 nm long pass filter. Images were captured every 5 µm through the 3D scaffolds with a field of view of 8,464 µm$^2$. Data acquisition was performed in SimFCS (software developed by the LFD). The images were analyzed using ctFIRE MATLAB software by extracting information corresponding to the fiber width and number. The data were collected from 3 separate z-stacks for each sample.

Example 4

Statistical Analysis

Split-Unit ANOVA was used to analyze qRT-PCR data using R analysis ($^\delta p > 0.05$ $^{\delta\delta} p > 0.01$). Figures show the standard error of the mean with n=3 unless otherwise stated. Student's T-test was performed on GCaMP calcium transients and standard error of the mean is shown. (*p<0.001, p<0.01, *p<0.05)

Example 5 iPSC-Derived Cardiomyocyte Maturation 2D cultures: Prior to seeding the iPSC-derived cardiomyocytes (Day 28-64 post induction), tissue culture plates were coated with 1 mg/ml of fetal or adult bovine cardiac extracellular matrix at 37° C. overnight. The cells were harvested with 200 Units/ml collagenase II (LifeTechnologies) for 1 hour, followed by 3× washes with PBS (Ca/Mg free), 5 min incubation in 10× TrypIE (LifeTechnologies) and then seeded at 45,000 cells/cardiomyocytes$^2$.

3D cultures: The cardiac extracellular matrix was adjusted to pH 7.4 with 0.1N NaOH and supplemented with ⅑ volume with 10×PBS (with Ca/Mg). The 3D scaffolds were composed of 5.25 mg/ml cardiac extracellular matrix and 1.75 mg/ml fibrinogen (Sigma). The cells were seeded at 1.6-3×10$^6$ cells/ml. The 3D gels were polymerized by the addition of 1.3 Units/ml thrombin (Sigma) and incubation at 37° C. for 2 hours before media was added. Each 3D tissue construct also contained 0.15 U/mL aprotinin (Sigma) in a total scaffold volume of 75 µl. Completed 3D gels were cultured in polydimethylsiloxane (PDMS, Dow Corning, Midland, Mich.) retention rings, each with a diameter of 8 mm and an approximate height of 1 mm. Cells were harvested after 7 days by digesting the tissue constructs with 500 Units/ml Collagenase II for 35-45 min.

Three independent biological experiments of the maturation studies were performed with each experiment using cardiac extracellular matrix from independent batch preparations and cardiac differentiations.

Example 6

Quantitative RT-PCR

Total RNA was harvested from differentiated iPSC using Trizol (Life Technologies) according to the manufacturer's recommended protocol and was treated with RQ1 DNAse (Promega, Madison, Wis.) for 1 hour. Three micrograms of RNA was used to generate cDNA using iScript cDNA Synthesis Kit (BioRad, Hercules, Calif.). qPCR was performed using SYBR green chemistry and an iQ5 BioRad icycler. mRNA levels were normalized to 18S expression and measured in triplicate. Primers were synthesized by Integrated DNA Technologies (Coralville, Iowa) and their sequences can be found in Table 1.

TABLE 1

Quantitative RT-PCR primer sequences.

| Gene Name | Sequence 5'->3' | SEQ ID |
|---|---|---|
| Junctin FWD | ATT GCA TTG CTG GGC GTC TG | SEQ ID NO: 1 |
| Junctin REV | GGC ATC ATC CAC ATC AAA ATC TCC | SEQ ID NO: 2 |
| MYL2 FWD | AGC GGA CCC TGA GGA AAC CAT T | SEQ ID NO: 3 |
| MYL2 REV | GGG AAG GCG GCG AAC ATC T | SEQ ID NO: 4 |
| NCX1 FWD | GTC CAT CGC TGC CAT CTA CCA C | SEQ ID NO: 5 |
| NCX1 REV | TAC AGC AGC ACC CCA CA TTG A | SEQ ID NO: 6 |
| Cx43 FWD | TCC CCT CTC GCC TAT GTC TCC TC | SEQ ID NO: 7 |
| Cx43 REV | CTG CCC CAT TCG ATT TTG TTC TG | SEQ ID NO: 8 |
| CaV1.2 FWD | ACA AGG GCC CCA TCT ACA ACT ACC | SEQ ID NO: 9 |
| CaV1.2 REV | CGA TGA CGA AGC CCA CGA AGA T | SEQ ID NO: 10 |
| 18S FWD | CCC CGG CCG TCC CTC TTA | SEQ ID NO: 11 |
| 18S REV | CGC CCC TCG ATG CT CTT AG | SEQ ID NO: 12 |
| Triadin FWD | AGA GCC CCC AGG TTT TGA CAC A | SEQ ID NO: 13 |
| Triadin REV | CGG GGG ATT TGG GCA CAG | SEQ ID NO: 14 |
| CASQ2 FWD | GTG GCC CAG GTC CTT GAA CAT AAA | SEQ ID NO: 15 |
| CASQ2 REV | GCT GCA AAC TCG CCA TCA AAC TCT | SEQ ID NO: 16 |

Tables 2A-E. SDS concentration used to decellularized cardiac tissue affects polymerization of fetal and adult bovine cardiac extracellular matrix.

TABLE 2A

Fetal cardiac ECM hydrogel. 1% SDS

| | 1% SDS | | | | |
|---|---|---|---|---|---|
| | 1 hour | | 2 hour | | Day 3 |
| | 50 µL | 75 µL | 50 µL | 75 µL | 100% |
| 16 mg/mL | — | — | Gel | Watery | decellularized |
| 12 mg/mL | — | — | — | — | |
| 10 mg/mL | — | — | — | — | |
| 7 mg/mL | — | — | — | — | |

TABLE 2B

Fetal cardiac ECM hydrogel. 0.5% SDS

| | 1% SDS | | | | |
|---|---|---|---|---|---|
| | 1 hour | | 2 hour | | Day 3 |
| | 50 µL | 75 µL | 50 µL | 75 µL | 90% |
| 16 mg/mL | Gel | Gel | Gel | Gel | decellularized |
| 12 mg/mL | — | — | Gel | Gel | |
| 10 mg/mL | — | — | Watery | Watery | |
| 7 mg/mL | — | — | Watery | Watery | |

TABLE 2C

Fetal cardiac ECM hydrogel. 0.25% SDS

| | 1% SDS | | | | |
|---|---|---|---|---|---|
| | 1 hour | | 2 hour | | Day 3 |
| | 50 µL | 75 µL | 50 µL | 75 µL | 80% |
| 16 mg/mL | Gel | Gel | Gel | Gel | decellularized |
| 12 mg/mL | — | — | Gel | Gel | |
| 10 mg/mL | — | — | Gel | Watery | |
| 7 mg/mL | — | — | Watery | Watery | |

TABLE 2D

Fetal cardiac ECM hydrogel. 0.1% and 0.05% SDS

| | 1% SDS | | | | |
|---|---|---|---|---|---|
| | 1 hour | | 2 hour | | Day 3 |
| | 50 µL | 75 µL | 50 µL | 75 µL | <70% |
| 16 mg/mL | Gel | Gel | Gel | Gel | decellularized |
| 12 mg/mL | Gel | Gel | Gel | Gel | |
| 10 mg/mL | — | — | Gel | Gel | |
| 7 mg/mL | — | — | Watery | Watery | |

TABLE 2E

Adult cardiac ECM hydrogel. 1% SDS

| | 1% SDS | | | | |
|---|---|---|---|---|---|
| | 1 hour | | 2 hour | | 2-3 days |
| | 50 µL | 75 µL | 50 µL | 75 µL | 100% |
| 16 mg/mL | Gel | Gel | Gel | Gel | decellularized |
| 12 mg/mL | Gel | Gel | Gel | Gel | |
| 10 mg/mL | Gel | Gel | Gel | Gel | |
| 7 mg/mL | Gel | Gel | Gel | Gel | |

Example 7

Calcium Imaging and Analysis

The iPSC-derived cardiomyocytes have been engineered to express a calcium indicator (GCaMP6f reporter) that emits fluorescence in the presence of cytosolic calcium. Calcium transients were measured using an epifluorescent microscope with an inverted 10× objective (IX70 Olympus, Tokyo, Japan). Images were captured using a SPOT Idea 3.0 megapixel color fluorescent camera and SPOT acquisition software (SPOT Imaging Solutions, Sterling Heights, Mich.). The cells were placed in a 37° C. heated stage during imaging. The video was captured at 33 frames/second with 8×8 binning. ImageJ was used to process and extract the temporal fluorescence intensity of the acquired video data.

Subsequent data were analyzed using MATLAB software (MathWorks, Torrance, Calif.). A customized algorithm determined the troughs and peaks of each calcium wave and measured the amplitude, max upslope, max downslope, time to 50% decay, and beat rate. Additional measurements included the effect of caffeine on the slope of amplitude change.

Example 8

Pharmacological Treatment of Cardiomyocytes

Baseline and drug recordings were taken before and after 10 min incubation with the drug(s) on the 37° C. stage. All recordings were taken over 1 min. The order of the β-adrenergic drug treatments was baseline, 1 µM isoproterenol (Sigma #16504), and 1 µM Isoproterenol+10 µM Propranolol (Sigma # P0884). The effect of caffeine (Tocris #2793) on calcium signaling was assessed at a final concentration of 20 mM. The video recordings were acquired before and during the addition of caffeine.

Example 9 nanoLC-MS MS

Decellularized fetal and adult tissue pellets were fully solubilized in a buffer comprising 4% SDS, 10 mM TCEP, 100 mM TEAB through repeated cycles of heating (95° C.)/ultrasonication (40° C.) followed by 120 min of ultrasonication. Protein levels were subsequently quantitated using the BCA assay. Equivalent mass amounts of the resulting samples were treated with iodoacetamide and trypsinized as described with modifications, and the resulting peptides desalted using stacked C18/SCX tips. The resulting peptides from each sample individually were subjected to nanoLC-MS/MS using an LTQ Orbitrap Velos Pro mass analyzer (Thermo Fisher Scientific, Waltham, Mass.) connected to a nanoLC-Easy1000, with peptide separation in an in-house-packed 25 cardiomyocytes×75 µm ID C18 nanospray tip. Peptides were resolved in segmented solvent gradients running from 6 to 35% $CH_3CN$ in 0.1% formic acid over 135 min. FTMS precursor spectra were acquired at 60,000 resolution, and up to 20 of the most intense ions with charge states of +2 and higher in each precursor spectrum were subjected to rapid CID fragmentation and ion trap analysis.

Spectral data were re-calculated using Mascot Distiller 2.5.0 (Matrix Science, Boston, Mass.) and the resulting peaklists were searched against SwissProt (July 2014) with *Bos Taurus* taxonomy along with a database of common contaminants using Mascot Server 2.5.0 (Matrix Science), with Carbamidomethyl (C) and Oxidation (M) as fixed and variable modifications, respectively, and precursor and fragment mass tolerances of 10 ppm and 0.5 Da, respectively. Homology false discovery rates were either below, or thresholded at 5%. Mascot protein score and emPAI values in Mascot exports were compared between samples using in-house software.

Example 10

Mechanical Analysis of 3D Cardiac Extracellular Matrix Hydrogels

Parallel plate rheology was conducted using an MCR 302 (Anton Paar, Ashland, Va.) to determine the storage and loss moduli (reported as pascals, Pa) of fetal and adult 3D cardiac extracellular matrix hydrogels composed of 5.25 mg/ml cardiac extracellular matrix and 1.75 mg/ml fibrinogen. Hydrogels were polymerized similar to the above experiments with measurements occurring after the two-hour incubation period at 37° C. Heating was conducted within a P-PTD200 Peltier-temperature-controlled hood (Anton Paar). The storage modulus (G') and loss modulus (G'') was measured at oscillation frequencies ranging from 0.1 to 10 Hz, with a constant strain amplitude of 1%. Experiments were conducted with a gap height of 200 µm using a 25-mm parallel plate. Each of the respective samples was measured in triplicate (n=3).

Example 11

Flow Cytometry

Cells were fixed with 4% PFA for 10 min and then incubated in 0.75% saponin in PBS. Samples were stained with 1:100 anti-cTNT antibody (ThermoScientific) or isotype control mouse IgG and subsequently incubated with goat anti-mouse FITC secondary antibody. Samples were run on a BD FACSCalibur flow cytometer and data were analyzed using FlowJo software.

Example 12

Immunocytochemistry

Cells were fixed with 4% paraformaldehyde for 30 min, permeabilized with 0.5% TritonX100, and then blocked with 0.1% Triton X-100 and 4% bovine serum albumin (blocking buffer). Cells were incubated in primary antibodies: 1:100 MYL2 (ProteinTech, Illinois), 1:100 CaV1.2 (Thermo-Fisher) and 1:800 α-actinin (Sigma-Aldrich) at 4° C. overnight, followed by secondary Alexa Fluor 488/568 for 2 hours in blocking buffer. Cell nuclei were subsequently stained with DAPI for 30 min. The cells were imaged with either an epifluorescent microscope (Nikon Eclipse TE300) or a confocal laser microscope (Leica TCS SP8).

Example 13

Hydrogel Encapsulation of Human iPS-Cardiomyocyte Spheroids iPSC-derived cardiomyocytes were seeded into AggreWell 400 (STEMCELL Technologies) at 720,000 cells per well. Cardiomyocyte spheroids were allowed to aggregate and self-assembled for two days before encapsulation within extracellular matrix.

Extracellular matrix hydrogels consisted of 10 mg/mL bovine fibrinogen (Sigma-Aldrich) dissolved in Dulbecco's phosphate buffered saline (Life Technologies) and combined with 9 mg/mL rat tail collagen (BD Biosciences) and 10 mg/mL cardiac extracellular matrix. All matrices denoted as a partial percentage had the remaining volume completed with fibrin. Thrombin was mixed with the cell and extracellular matrix solution to yield a final concentration of 3 Units/mL (0.3 Units/mg fibrin). Spheroids resuspended in extracellular matrix mixture were cultured in three PDMS retention rings attached to a glass bottom dish (World Precision Instruments, Sarasota, Fla.). The tissues were incubated for 30 min at 37° C. to allow full polymerization, and then fed RPMI 1640 supplemented with B27. The medium was replaced every 2 days.

Example 14

Figure 6:
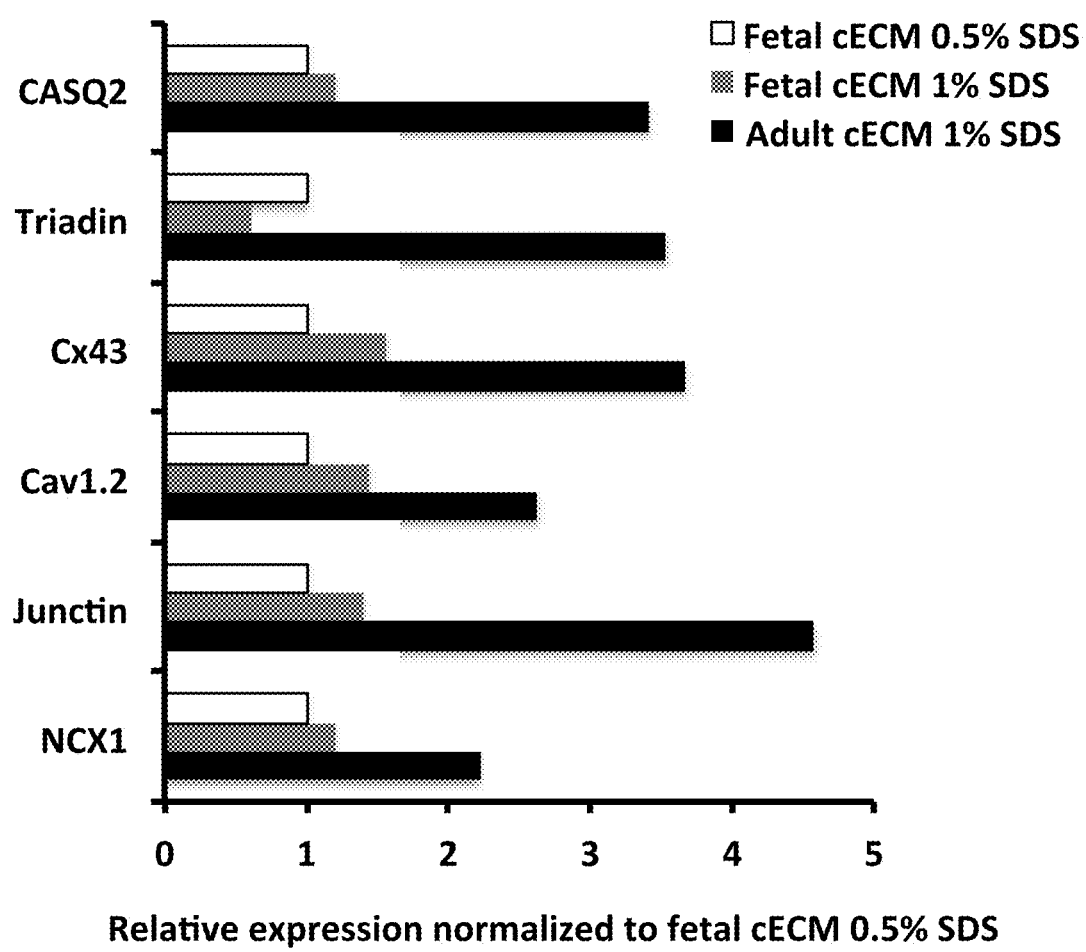
FIG. 6 illustrates, in accordance with embodiments herewith, that the induction of iPSC-derived cardiomyocyte cardiac genes is indistinguishable on gels derived from fetal tissues decellularized with 0.5 and 1% SDS. Cardiac genes were measured using qRT-PCR and expression normalized to 2D fetal cardiac extracellular matrix decellularized with 0.5% SDS. The cardiac genes measured were Triadin, Junctin, CACNA1C/CaV1.2 (L-type voltage-dependent calcium channel), Cx43 (connexin-43), CASQ2 (calsequestrin 2), NCX1 (sodium-calcium exchanger 1). Comparing expression from iPSC-derived cardiomyocytes cultured for 7 days on 2D fetal cardiac extracellular matrix decellularized with 0.5% and 1% SDS to 2D adult cardiac extracellular matrix.

Characterization of Extracellular Matrix from Decellularized Adult and Fetal Bovine Cardiac Tissue To investigate the potential differences between fetal and adult cardiac extracellular matrix and their respective contributions to human iPSC-derived cardiomyocyte maturation, cardiac extracellular matrix was isolated through sodium dodecyl sulfate (SDS)- and Triton-X100 detergent-mediated decellularization of fetal and adult bovine heart muscle. In one embodiment similar polymerization characteristics were obtained using 1% SDS for the adult tissue and 0.5% SDS for the fetal tissue (Table 2). In another embodiment, as illustrated in FIG. 6, the fetal cardiac extracellular matrix decellularized with either 0.5% or 1% SDS induced a similar gene expression profile compared to adult cardiac extracellular matrix when used in 2D assays. H&E staining confirmed the removal of cells during the decellularization process, as illustrated in FIG. 1.

Figure 7:
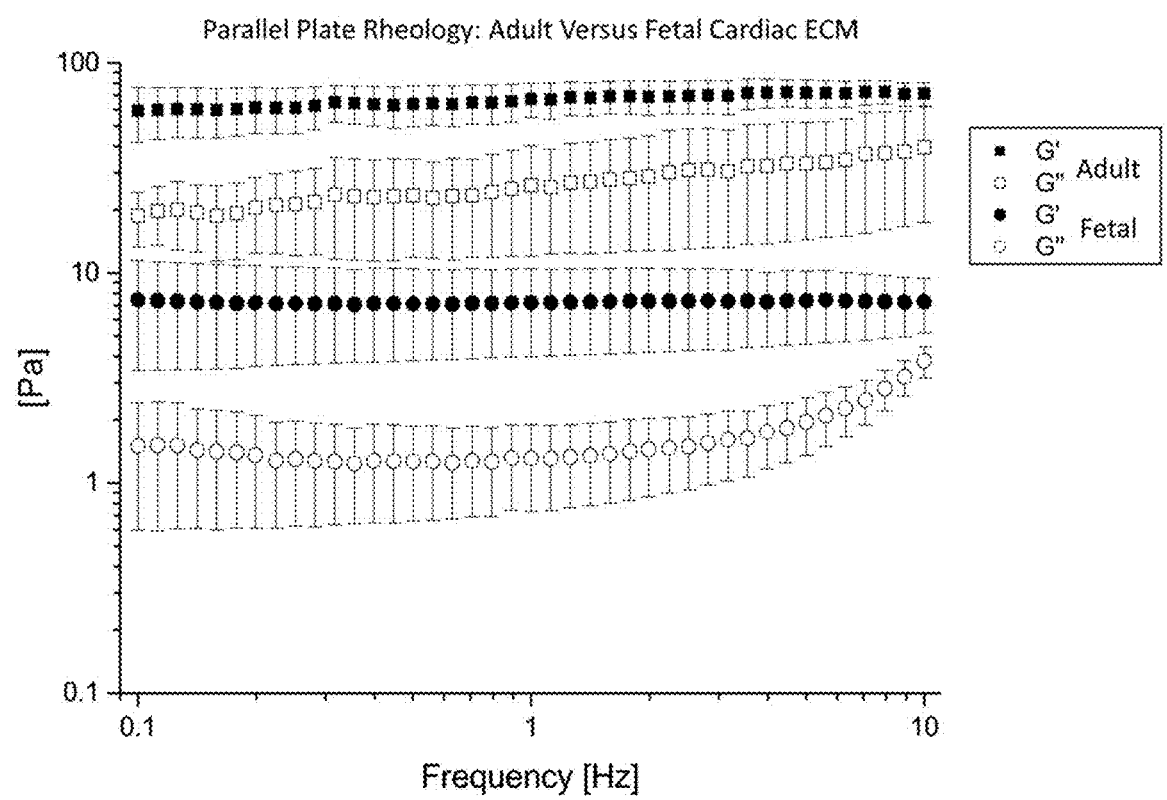
FIG. 7 illustrates, in accordance with embodiments herewith, that adult cardiac extracellular matrix hydrogels have higher storage and loss modulus compared to fetal hydrogels. Parallel plate rheology was used to quantify the storage and loss moduli of each sample. A frequency sweep was performed at a strain amplitude of 1% from 0.1 to 10 Hz. Results are expressed as mean±standard error for each frequency. (n=3)

The protein compositions of fetal and adult cardiac extracellular matrix were characterized by nano-LC MS/MS. At the score thresholds employed, the prominent proteins were fibrinogen, collagen, periostin, fibrillin, fibulin, fibronectin and other matrix proteins (Table 3). The fetal cardiac extracellular matrix samples contained two unique proteins not found in the adult samples, mimecan and versican (Table 3). In one embodiment, to examine the structure and distribution of collagen and elastin within the extracellular matrix, second harmonic generation (SHG) was used to detect collagen fibers and auto-fluorescence to detect elastin fibers. The elastin fibers of the fetal extracellular matrix, prior to pepsin digestion, were more evenly distributed, while there were more defined, organized bundles in the adult extracellular matrix (FIG. 1, panels E, F). In contrast to fetal extracellular matrix, the decellularized adult cardiac extracellular matrix displayed a higher collagen fiber signal intensity and larger bundles evident by increased fiber width and number (FIG. 1, panels G-J). Hydrogels were formed with the adult and fetal cardiac extracellular matrix, and storage modulus (G') and loss modulus (G") were measured by parallel plate rheology. The adult cardiac extracellular matrix (67.5±12.6 Pa) was ~10-fold stiffer than fetal cardiac extracellular matrix (7.2±3.2 Pa) (Table 4, FIG. 7).

TABLE 3

Key proteins identified in decellularized adult and fetal bovine heart tissue preparations by nanoLC-MS/MS. Data were thresholded at 4.4% and 4.8% FDR for adult and fetal samples, respectively.

|  | Bovine Heart | |
| --- | --- | --- |
|  | Fetal | Adult |
| Fibrinogen | x | x |
| Collagen IV | x | x |
| Periostin | x | x |
| Fibrillin-1 | x | x |
| Collagen III | x | x |
| Lumican | x | x |
| Fibronectin | x | x |
| Fibulin-5 | x | x |
| Mimecan | x |  |
| Collagen I | x | x |
| Decorin | x | x |
| Fibulin-1C | x | x |
| Elastin | x | x |
| Dermatopontin | x | x |
| Versican | x |  |

TABLE 4

Mechanical properties of fetal and adult cardiac extracellular matrix hydrogels. Parallel plate rheology was used to determine storage and loss modulus at an oscillation rate of 1 Hz with 1% strain amplitude. Results are expressed as mean ± standard error.

| Source (3D Hydrogel) | Storage Modulus (G', Pa) | Loss Modulus (G", Pa) |
| --- | --- | --- |
| Fetal (n = 3) | 7.2 ± 3.2 | 1.3 ± 0.58 |
| Adult (n = 3) | 67.5 ± 12.6 | 26.2 ± 14.1 |

Example 15

Figure 2:
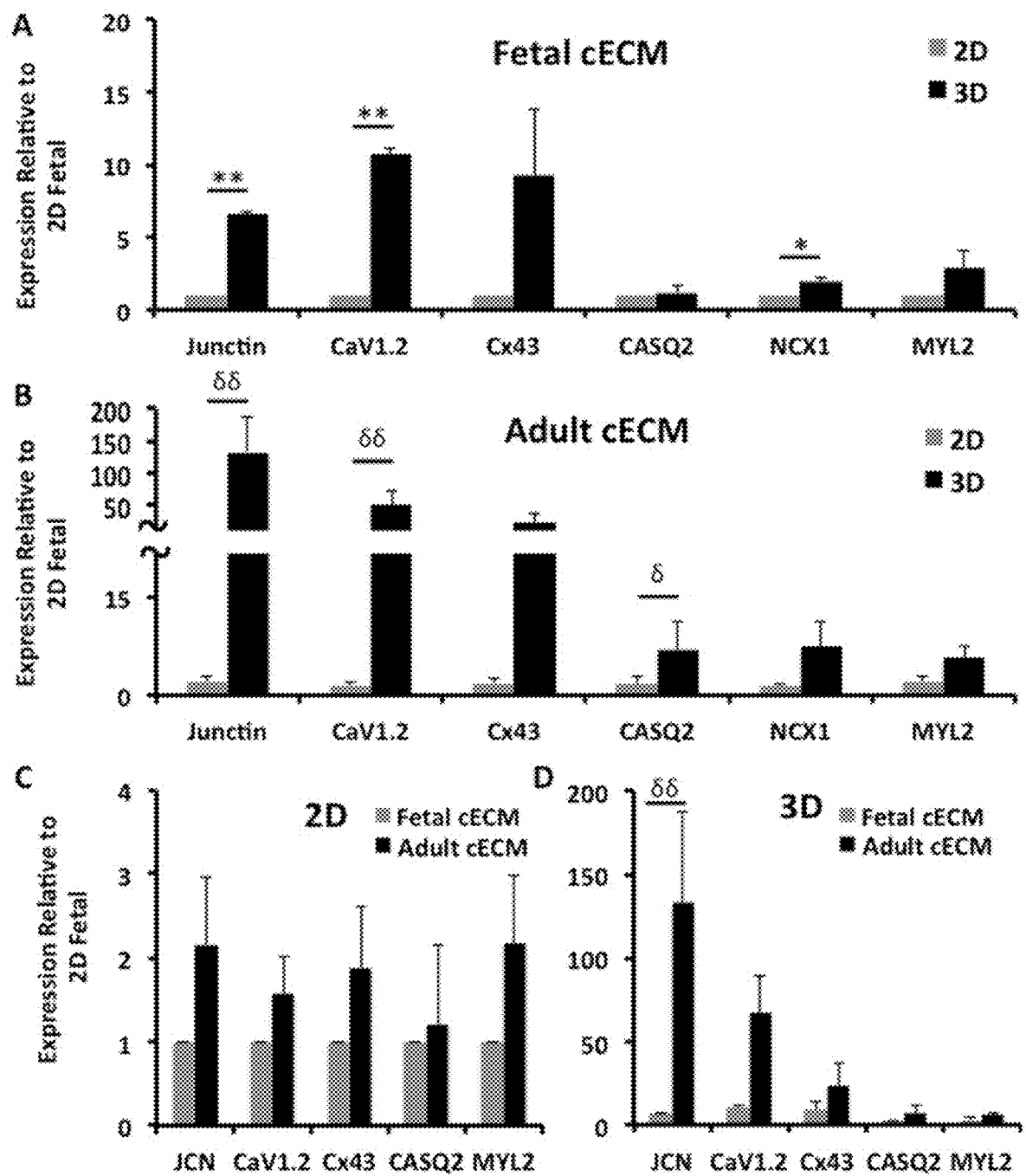
FIG. 2 illustrates, in accordance with embodiments herewith, one embodiment of the present disclosure where 3D adult cardiac extracellular matrix increases iPSC-derived cardiomyocyte expression of structural and functional cardiac genes. Gene expression was measured using qRT-PCR and expression normalized to 2D fetal cardiac extracellular matrix. Cardiac genes measured were JCN (Junctin), CACNA1C/CaV1.2 (L-type voltage-dependent calcium channel), Cx43 (connexin-43), CASQ2 (calsequestrin 2), NCX1 (sodium-calcium exchanger 1), and MYL2 (myosin light chain 2). Panel A illustrates gene expression in iPSC-derived cardiomyocytes cultured in 3D or on 2D fetal cardiac extracellular matrix. (*$p>0.01$ **$p>0.001$, Student's T-test). Panel B illustrates gene expression in iPSC-derived cardiomyocytes cultured in 3D or on 2D adult cardiac extracellular matrix. Panels C and D illustrates data from panels A and B, which are re-plotted to aid direct comparison of gene expression in iPSC-derived cardiomyocytes cultured on adult and fetal 2D cardiac extra cellular matrix and 3D cardiac extra cellular matrix, respectively. Unless otherwise indicated, results are expressed as mean±standard error. (n=3; $^\delta p>0.05 {}^{\delta\delta}p>0.01$, Split-Unit ANOVA)

3D Adult Cardiac Extracellular Matrix Promotes Expression of Cardiomyocytes Maturation Genes In order to determine if cardiac extracellular matrix affects iPSC-derived cardiomyocytes maturation gene expression (by qPCR) in cells cultured in 2D and 3D fetal and adult cardiac extracellular matrix was examined. After 7 days in culture, iPSC-derived cardiomyocytes seeded into 3D cardiac extracellular matrix (from fetal or adult tissue) expressed higher levels of numerous maturation-related genes compared to cells in 2D gels. These included genes related to calcium handling, such as Junctin (JCN), L-type voltage-dependent calcium channel (CACNA1C/CaV1.2), calsequestrin 2 (CASQ2), and sodium-calcium exchanger 1 (NCX1), which were augmented between 2 and 120-fold, as illustrated in FIG. 2 panels A and B. In one embodiment, similar increases in expression of several other genes related to cardiac maturation was seen, including Triadin (88-fold; n=2), sarcoplasmic reticulum Ca2+ ATPase (SERCA2a) (30-fold; n=1), and potassium/sodium hyperpolarization-activated cyclic nucleotide-gated channel 4 (HCN4) (7-fold; n=1) in 3D versus 2D culture. In one embodiment, there was strong induction of these same genes, such as JCN, when comparing adult to fetal matrix, with the augmentation being particularly marked in 3D cultures, as illustrated in FIG. 2, panels C, D.

Figure 3:
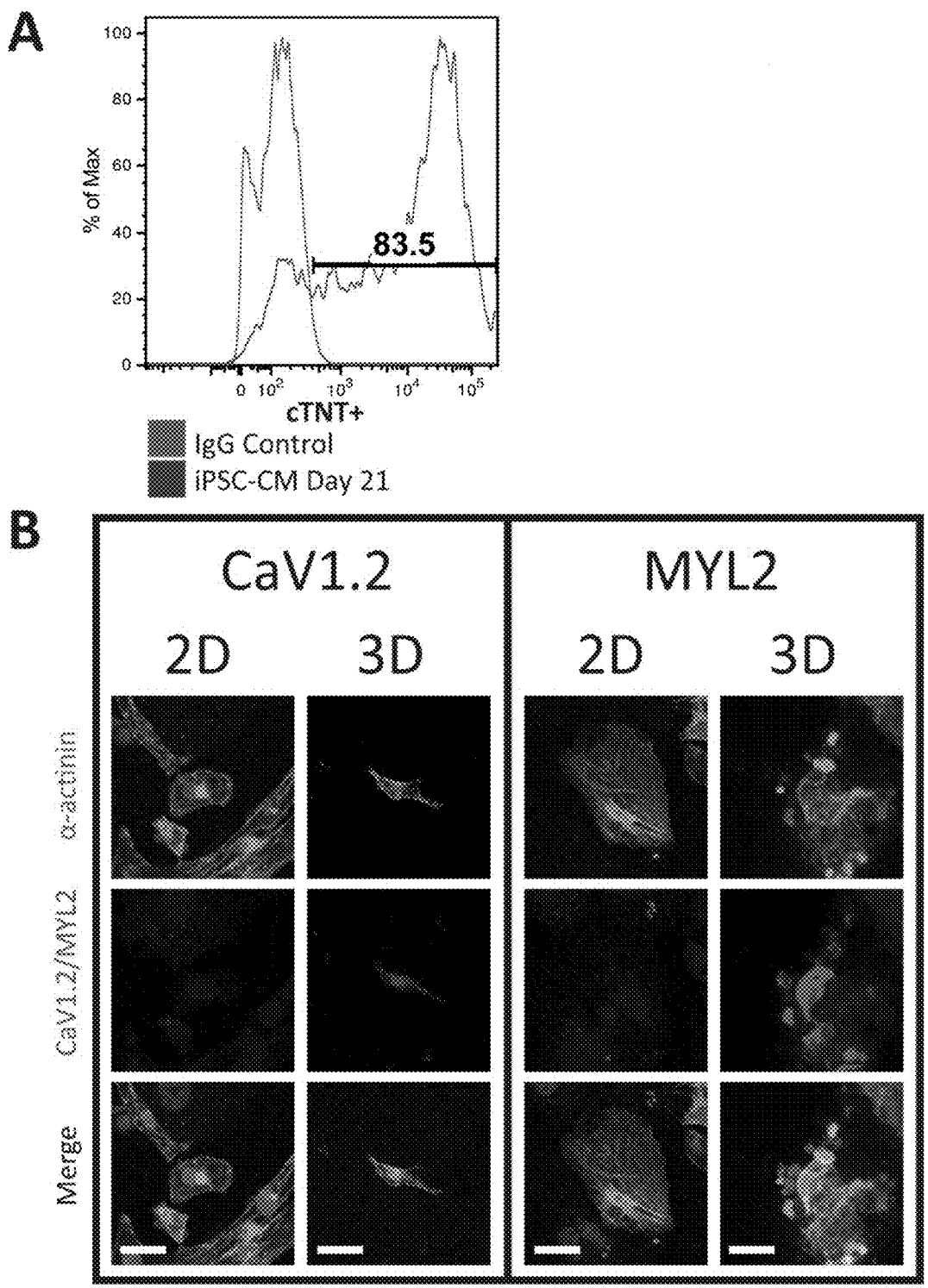
FIG. 3 illustrates, in accordance with embodiments herewith, 3D adult cardiac extracellular matrix increases iPSC-derived cardiomyocytes protein expression of structural and calcium handling proteins. iPSC-derived cardiomyocytes express sarcomere and calcium handling proteins. Panel A illustrates flow cytometry analysis for cTNT(+) cells after 21 days of differentiation. Panel B illustrates immunofluorescent staining for MYL2 and CaV1.2 in iPSC-derived cardiomyocytes cultured in 2D and 3D cardiac extracellular matrix. The right panels illustrate MYL2 staining, while the left panels illustrate CaV1.2 staining. Scale bar is 30 m.
Figure 8:
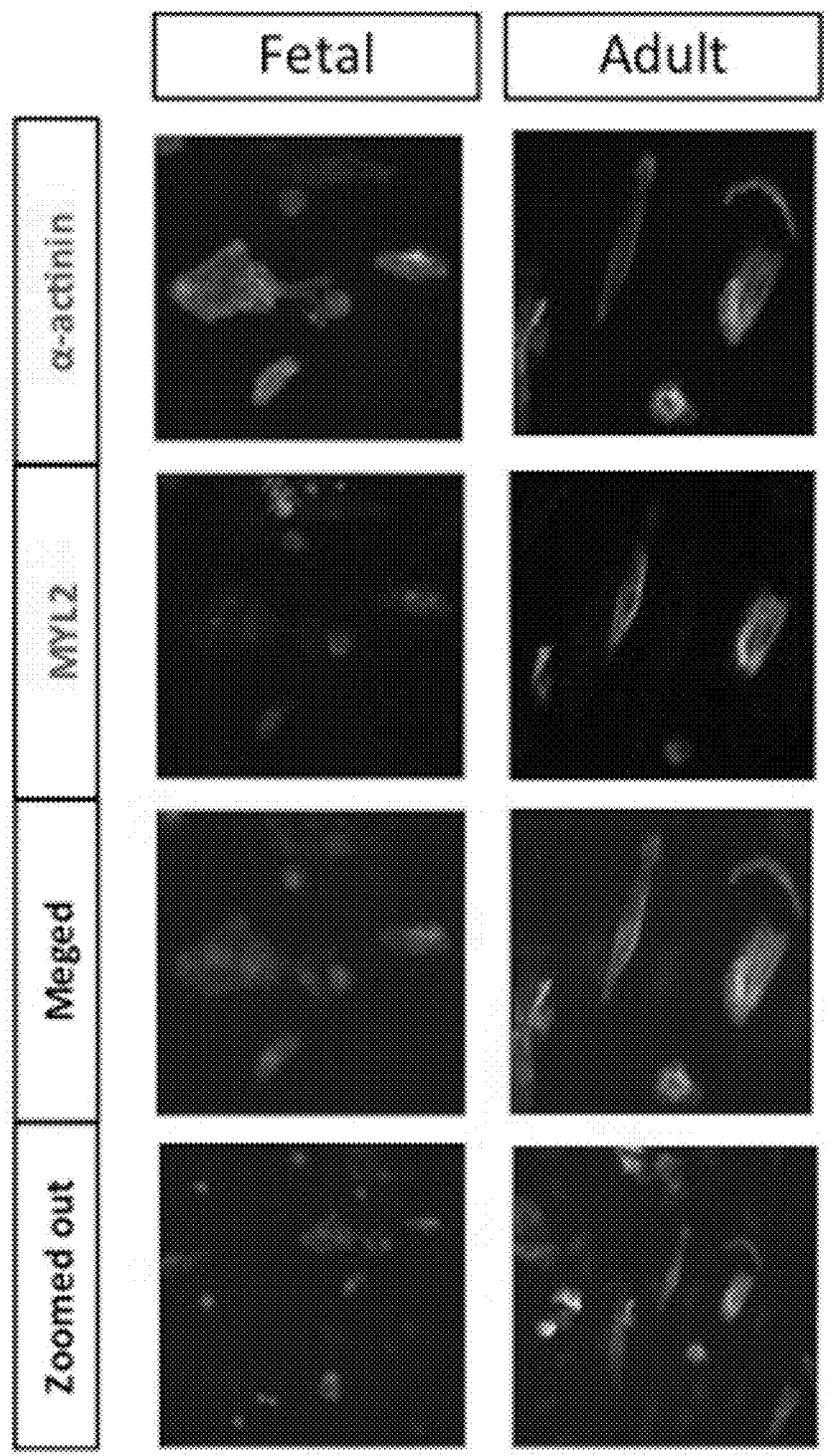
FIG. 8 illustrates, in accordance with embodiments herewith, that iPSC-derived cardiomyocytes cultured on adult cardiac extracellular matrix compared to fetal has increased protein expression of MYL2. Immunofluorescent staining of iPSC-derived cardiomyocytes cultured in 2D cardiac extracellular matrix for MYL2.

In one embodiment, the expression of key structural and calcium-handling genes at the protein level was examined. After 21 days of cardiac induction, 50-90% of differentiated cells expressed cardiac troponin T (cTNT), which is a marker of cardiomyocytes differentiation (FIG. 3, panel A). In one embodiment, a strong induction of CaV1.2 and MYL2 protein was found in iPSC-derived cardiomyocytes cultured in 3D adult cardiac extracellular matrix, compared to 2D (FIG. 3, panel B). In addition, the iPSC-derived cardiomyocytes cultured on adult cardiac extracellular matrix exhibited increased expression of MYL2 compared to cells on fetal extracellular matrix (FIG. 8). Thus, in one embodiment, both the source (fetal vs adult) and the geometry (2D vs 3D) of extracellular matrix strongly influences maturation of iPSC-derived cardiomyocytes.

Example 16

Figure 4:
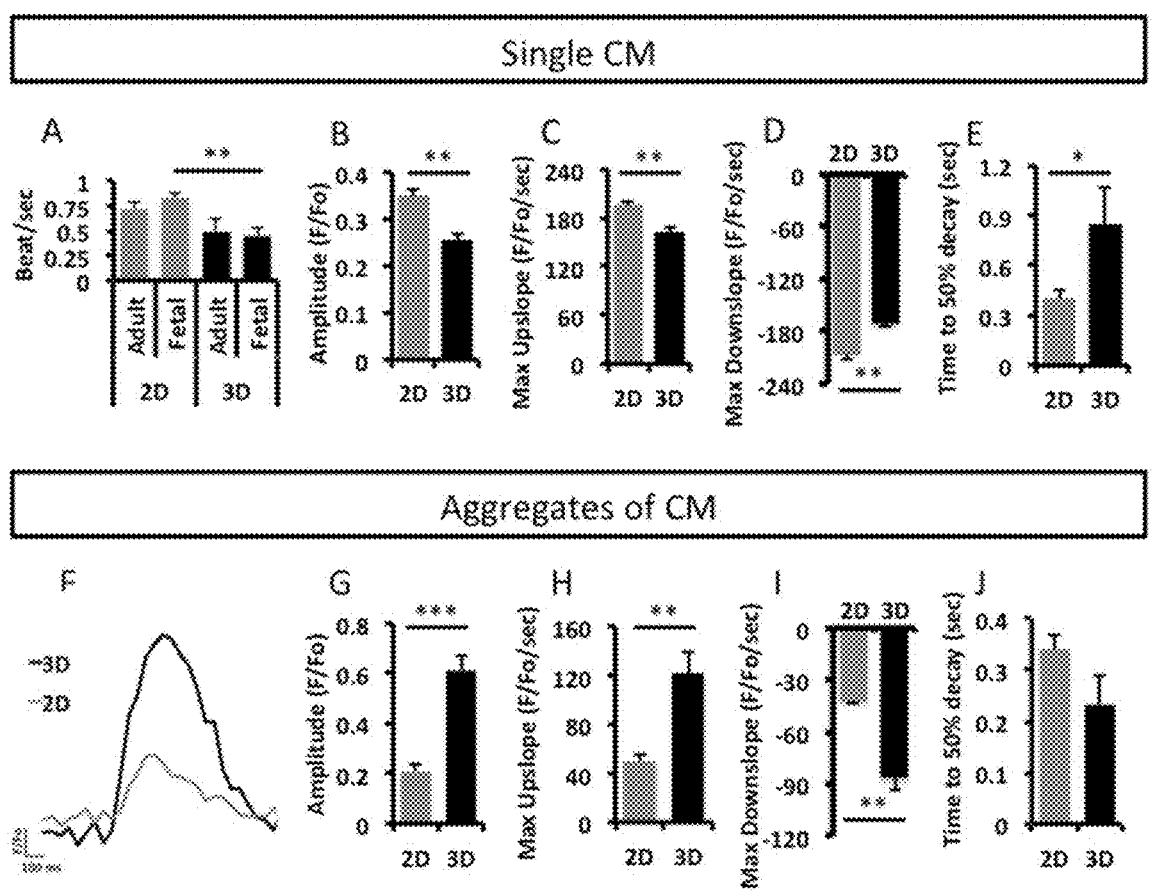
FIG. 4 illustrates, in accordance with embodiments herewith, 3D adult cardiac extracellular matrix increases calcium signaling in iPSC-derived cardiomyocytes. A GCaMP reporter was used to visualize calcium transients in iPSC-derived cardiomyocytes after 7 days in 2D and 3D adult cardiac extracellular matrix. Panels A-E illustrate iPSC-derived cardiomyocytes cultured in 3D as single cells displayed decreased calcium signaling and kinetics. Panels F through J illustrate iPSC-derived cardiomyocytes cultured in 3D as aggregates displayed an increase in calcium signaling and kinetics compared to 2D. Panel A illustrates representative beat rate of iPSC-derived cardiomyocytes cultured in 2D and 3D adult/fetal cardiac extracellular matrix. Panels B and G illustrates the amplitude; panels C and H illustrate Max Upslope; panels D and I illustrate Max Downslope; and panels E and J illustrate time to 50% decay. Panel F is a representative calcium wave transient of iPSC-derived cardiomyocytes culture in 2D and 3D adult cardiac extracellular matrix. Results are expressed as mean±standard error. (n=4-12; *$p<0.05$ $p<0.01$ *$p<0.001$, Student's t-test)

Cardiac Extracellular Matrix Geometry Affects iPSC-Derived Cardiomyocytes Calcium Signaling The genetically-encoded fluorescent calcium flux reporter GCaMP6 was utilized to assess the functional effects of extracellular matrix geometry on iPSC-derived cardiomyocytes calcium handling. Comparison of single cells in 2D culture with single cells embedded in 3D gels was performed. When cultured for 7 days in 3D cardiac extracellular matrix, the iPSC-derived cardiomyocytes showed a significant decrease in beat rate compared to 2D culture (FIG. 4, panel A). In some embodiments, decrease in calcium transient amplitude, maximum upslope, and maximum downslope, and a concomitant increase in time to 50% decay was observed (FIG. 4, panels B-E). In some embodiments, these data demonstrate a clear effect of matrix geometry on cardiomyocytes calcium handling. In vivo cardiomyocytes are in close association and the formation of syncitia promotes electrical coupling. To mimic this, aggregates of iPSC-derived cardiomyocytes were cultured in 3D gels and also allowed these to settle onto 2D gels. The calcium handling capabilities of the cells under these conditions was quite different from those seen when the cells are not in close association. Representative traces of calcium influx are shown in FIG. 4 panel F. Calcium transient amplitude, maximum upslope, and maximum downslope were all increased (they were decreased with single cells) and the time to 50% decay was correspondingly decreased when cells were in 3D versus 2D (FIG. 4, panels G-J). Beat rate was not significantly altered by matrix geometry.

Figure 9:
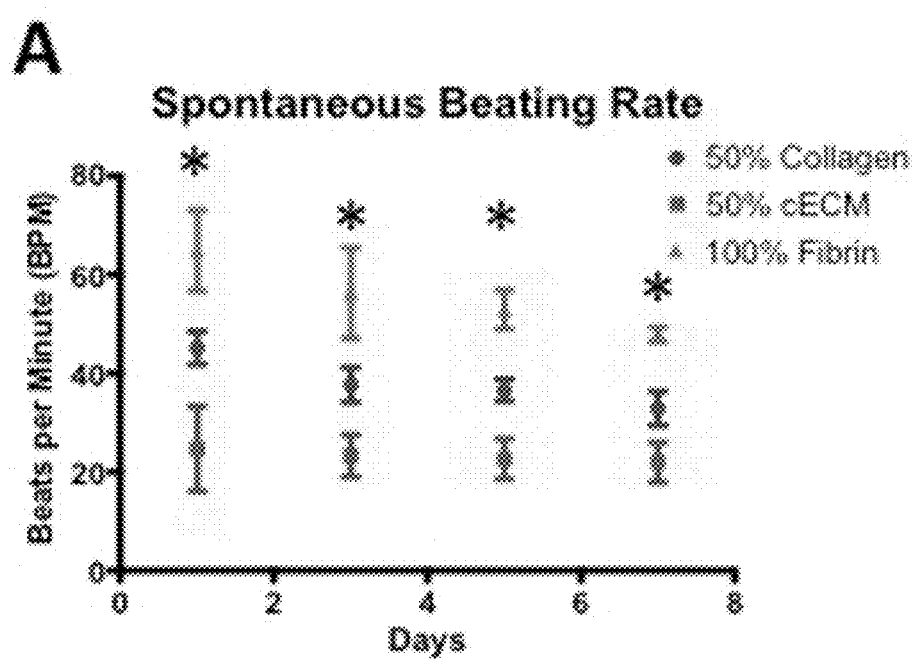
FIG. 9 illustrates, in accordance with embodiments herewith, that 3D adult cardiac extracellular matrix decreases iPSC-derived cardiomyocytes beat rate. Spontaneous beating rate significantly decreased with respect to time in culture and matrix composition. (*p<0.0001, two-way ANOVA)

In one embodiment, iPSC-derived cardiomyocytes behavior was examined in a third model—cardiac spheroids embedded in 3D hydrogels composed of either adult porcine cardiac extracellular matrix, fibrin, or collagen I. Compared to either fibrin or collagen I, cells in native cardiac matrix showed a decreased beat rate (FIG. 9). These data are consistent with the promotion of cardiomyocyte maturation by native heart matrix.

Example 17

Figure 5:
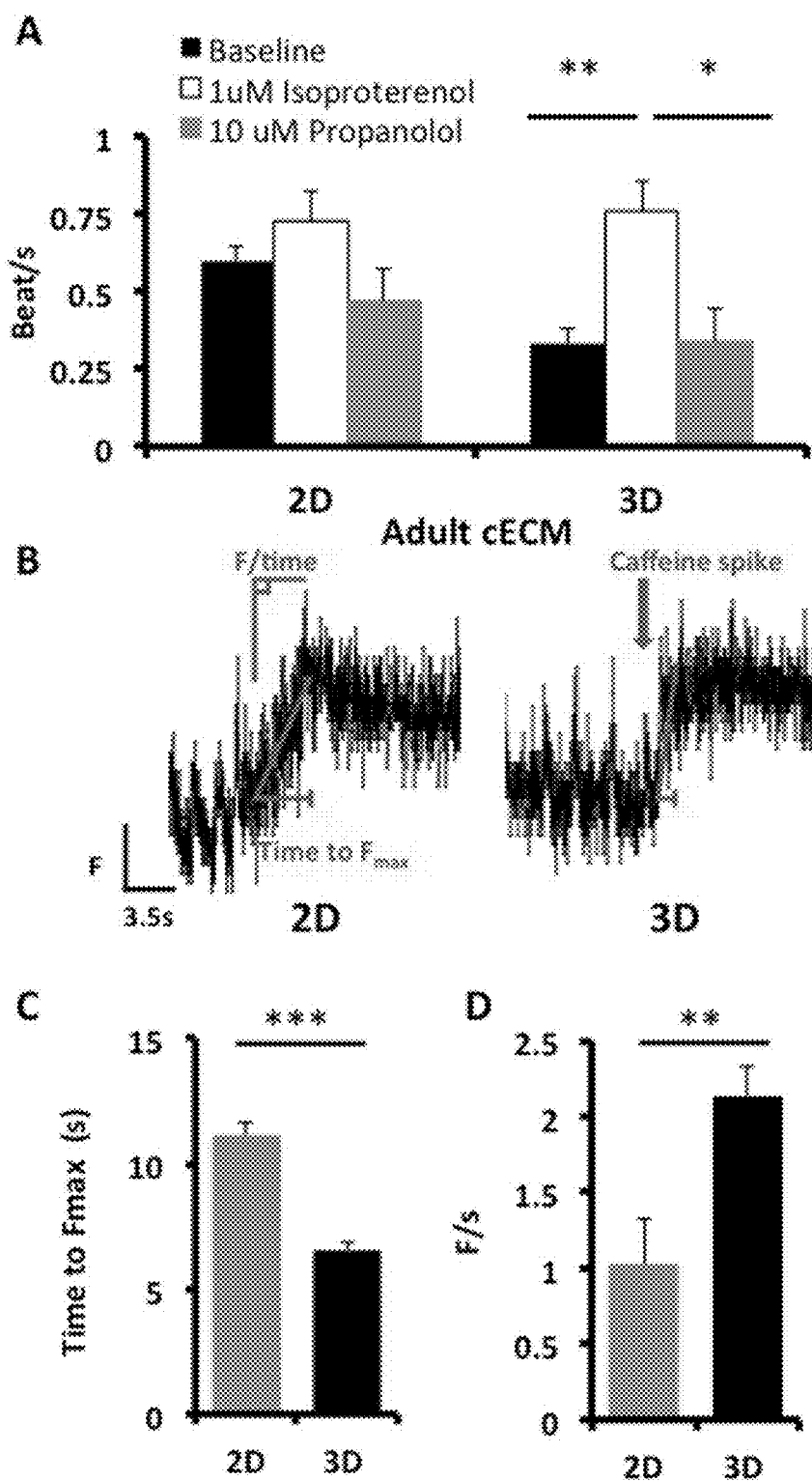
FIG. 5 illustrates, in accordance with embodiments herewith, 3D adult cardiac extracellular matrix increases iPSC-derived cardiomyocytes response to drugs. iPSC-derived cardiomyocytes cultured in 3D were more responsive to β-adrenergic stimuli and caffeine than cells in 2D cultures. Panel A illustrates the effect of isoproterenol and propranolol on the beat rate of iPSC-derived cardiomyocytes. Panel B illustrates a representative fluorescent signal of the iPSC-derived cardiomyocyte calcium transient in response to 20 mM caffeine cultured in 2D and 3D adult cardiac extracellular matrix. Panel C illustrates the time to maximum fluorescent output ($F_{max}$) was measured after the addition of caffeine. Panel D illustrates the velocity of calcium release F/time. Results are expressed as mean±standard error. (n=13-17; $p<0.01$ *$p<0.001$, Student's t-test)

3D Adult Cardiac Extracellular Matrix Increases iPSC-Derived Cardiomyocyte Response to Drugs To further assess the functionality of iPSC-derived cardiomyocytes in 3D cardiac extracellular matrix, cells were exposed to isoproterenol and propranolol, drugs known to modulate β-adrenergic signaling, and consequently, calcium handling. Consistent with the known behavior of adult cardiomyocytes, the iPSC-derived cardiomyocytes increased their beat rate upon the addition of 1 μM isoproterenol (FIG. 5A), and this was decreased to baseline levels following the addition of 10 μM propranolol (FIG. 5A). Caffeine targets the ryanodine receptor (RyR), resulting in an increase in available calcium. Exposure of iPSC-derived cardiomyocytes to caffeine resulted in a more rapid release of calcium in 3D culture than in 2D (FIG. 5B). The upslope was steeper and the time to maximum calcium concentration was quicker (FIG. 5C, D). Thus, in one embodiment, iPSC-derived cardiomyocytes are responsive to drugs with known cardiac effects and these effects are more pronounced in 3D versus 2D culture.

Example 18

Cardiac Differentiation

The WTC-11 GCaMP iPSC line was used in accordance with UC Irvine's Human Stem Cell Research Oversight Committee. iPSCs were maintained with mTeSR medium (StemCell Technologies) on Matrigel Growth Factor Reduced (BD) coated dishes. Cardiac differentiation was induced by glycogen synthase kinase-3 inhibition (CHIR99021, 6 μM, Tocris Inc) and Wnt inhibition (IWP2, 5 μM, Tocris).

Example 19

Endothelial Cell Isolation

Endothelial progenitor cells (ECs) were isolated from human umbilical cord blood through CD31(+) cell purification from the mononuclear cell fraction.

Example 20

EC Co-Culture and Condition Medium

EC and iPSC-derived CMs were plated onto Matrigel Growth Factor Reduced (BD) coated dishes. Cells were fed with RPMI media supplemented with B27 (Life Technologies) and Endothelial Cell Growth Supplement (ECGS; BD Biosciences) every 2-3 days. EC-conditioned medium was collected after 1-3 days of EC growth. Endothelin inhibition was achieved by adding 10 nM PD145065 inhibitor (EMD Millipore) and notch inhibition with 20 μM DAPT (Sigma) at every media change. Cells were fed on days 1 and 4 and then harvested after 7 days.

Example 21 gPCR

RNA was extracted using TRIzol (Life Technologies) according to manufacturer's instructions. Three micrograms of RNA was used to generate cDNA using the iSCRIPT cDNA Synthesis Kit (Bio-Rad). The reaction mix included SYBR green chemistry and primers generated by IDT Technologies. The samples were analyzed using an iQ5 Real Time PCR Detection System (Bio-Rad). The control sample, compared to EC/iPSC-derived CM co-culture, consisted of a mix of equal parts EC and iPSC-derived CM RNA that were isolated separately. (n=3; *$p<0.05$ $p<0.01$ *$p<0.001$, Student's t-test)

Example 22

Figure 10:
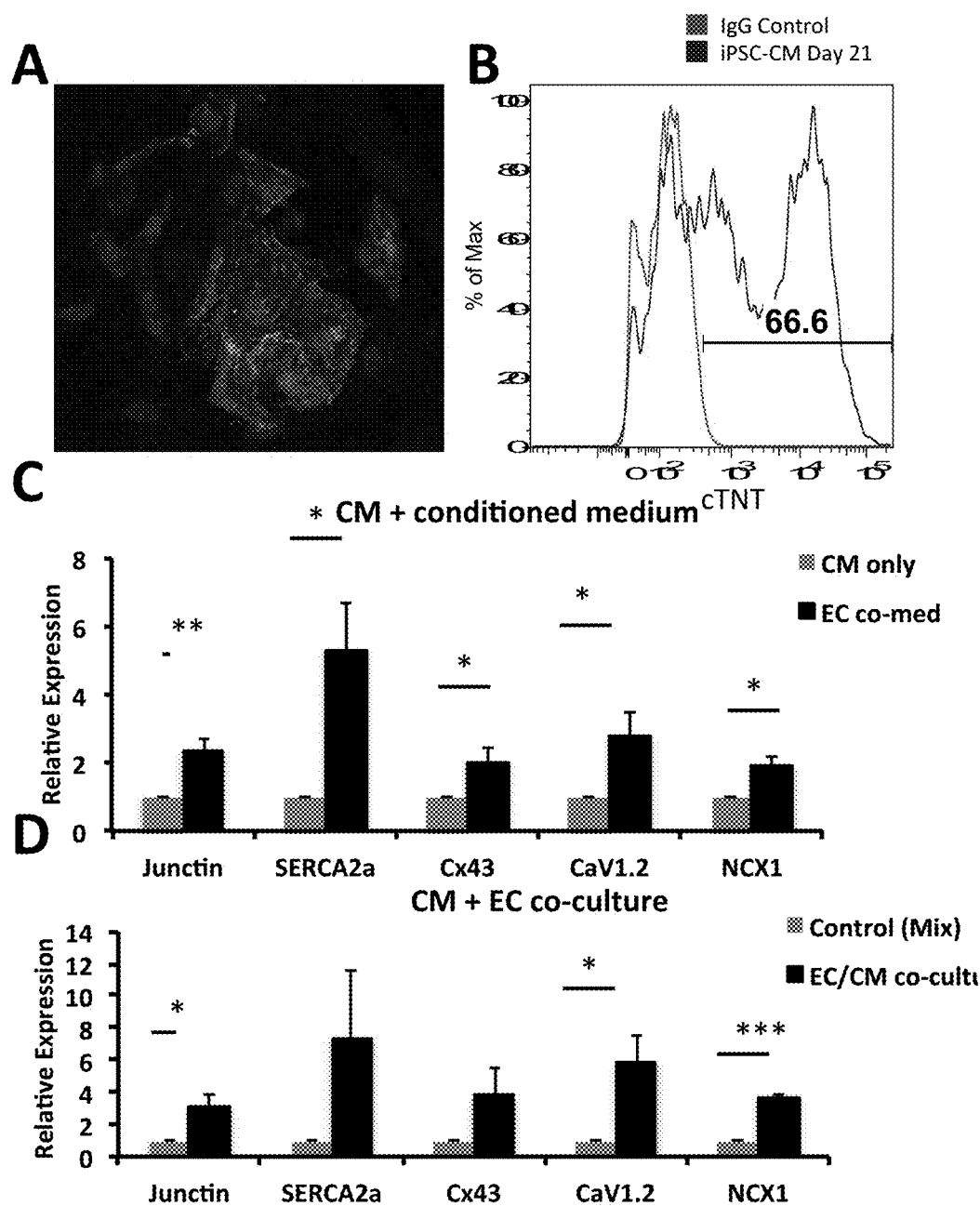
FIG. 10 illustrates, in accordance with embodiments herewith, that endothelial cells promote increased expression of cardiac maturation markers of iPSC-derived cardiomyocytes. Panel A illustrates immunofluorescent staining of iPSC-derived cardiomyocytes for α-actinin (green), myosin light chain 2V (red), and nuclei (blue). Panel B shows flow cytometry analysis for cTNT (+) cells after 21 days of differentiation. Panels C and D illustrate that endothetial cells promote iPSC-derived CM expression of functional and calcium handling genes. (C) qRT-PCR was used to measure gene expression after 7 days in culture with endothelial cells conditioned media. Measured cardiac genes include Junctin, SERAC2a (sarco/endoplasmic reticulum $Ca^{2+}$-ATPase 2a), Cx43 (connexin-43), CACNA1C/CaV1.2 (L-type voltage-dependent calcium channel), and NCX1 (sodium-calcium exchanger 1). (D) The effect of endothelial cells/cardiomyocytes co-culture on iPSC-derived cardiomyocytes gene expression after 7 days. (n=3; *p<0.05 **p<0.01, Student's t-test)

EC-Conditioned Media and EC Co-Culture Increases iPSC-Derived CM Gene Expression of Maturation Markers In one embodiment, in order to determine the effect of EC on CM maturation, the inventors differentiated iPSC into CMs using small molecule inhibitors for glycogen synthase kinase 3 and Wnt signaling. After 21 days, the iPSC-derived CMs were between 50-80% positive for cardiac troponin T (cTNT) (FIG. 10, panel A) and expressed the sarcomeric protein, α-actinin (FIG. 10, panel B). Next, the iPSC-derived CMs were cultured in EC conditioned medium for 7 days and gene expression of maturation markers were evaluated using qPCR. EC conditioned medium caused an increase in iPSC-derived CM expression of the gap junction and calcium handling genes, Junctin, sarco/endoplasmic reticulum $Ca^{2+}$-ATPase 2a (SERCA2a), connexin-43 (Cx43), L-type voltage-dependent calcium channel (CaV1.2), sodium-calcium exchanger 1 (NCX1) (FIG. 10, panel C). In addition, a 7 day co-culture of EC with iPSC-derived CM resulted in the upregulation of similar cardiac maturation markers, Junctin, SERCA2a, Cx43, CaV1.2, and NCX1 (FIG. 10, panel D). These results demonstrate that EC co-culturing and conditioned medium induce the iPSC-derived CM maturation as indicated by increased expression of maturation genes.

Example 23

Figure 11:
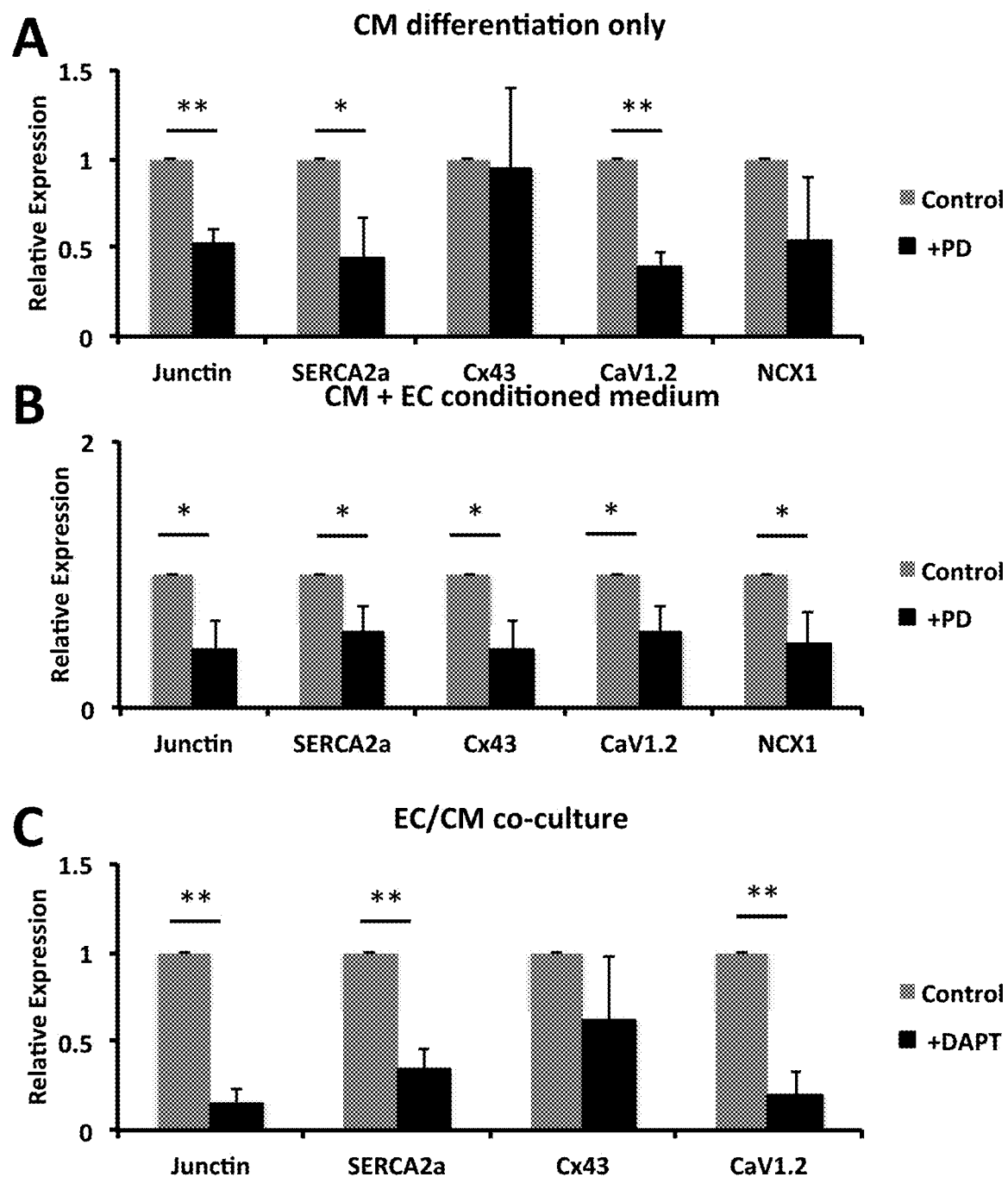
FIG. 11 illustrates, in accordance with embodiments herewith, inhibition of ET and notch signaling decreases iPSC-derived cardiomyocytes expression of calcium handling genes. The small molecule inhibitors, PD 142893 (ET) and DAPT (notch), were incubated with the iPSC-derived cardiomyocytes and after 7 days gene expression of maturation markers (Junctin, SERCA2a, Cx43, CaV1.2) was measured using qPCR. (A) The effect of PD 142893 (ET inhibition) on the iPSC-derived CM. (B). The effect of PD 142893, ET inhibition, on the iPSC-derived CM cultured in EC-conditioned medium. (C). The effect of DAPT on the iPSC-derived CM co-cultured with EC. (n=3; *p<0.05 **p<0.01, Student's t-test).

Inhibition of ET and Notch Signaling Decreases iPSC-Derived CM Gene Expression of Maturation Markers Induced by EC In one embodiment, to determine the mechanism by which EC induce iPSC-derived CM maturation, the inventors focused on the secreted protein ET and measured gene expression of CM maturation markers when cultured in EC conditioned medium. By using a 10 nM PD 142893, a non-selective endothelin receptor inhibitor, a decrease was found in maturation markers Junctin, SERCA2a, and CaV1.2 in the CM only control (FIG. 11, panel A) and Junctin, SERCA2a, Cx43, CaV1.2 and NCX1 in the EC condition medium condition (FIG. 11, panel B). Furthermore, the inhibition of notch signaling by DAPT, a gamma-secreatase inhibitor, resulted in the decrease in maturation markers, Junctin, SERCA2a, and CaV1.2 when the EC and CM are co-cultured (FIG. 2C). The inhibition of ET and notch signaling results in decreased expression of maturation markers thereby indicating their role in regulating CM maturation.

Example 24

Cardiomyocytes and Cardiac Extracellular Matrix

In one embodiment, the properties and composition of native cardiac extracellular matrix from adult and fetal bovine hearts were studied and tested their ability to promote iPSC-derived cardiomyocyte maturation in both 2D and 3D conformations. Using a 3D conformation was found to have several advantages compared to 2D cultures for the generation of iPSC-derived cardiomyocytes, notably that that the composition and stiffness of the 3D matrix conveys critical maturation signals to the developing cardiomyocytes.

While 2D studies to induce the maturation of pluripotent stem cell-derived cardiomyocytes have advanced the knowledge of cardiomyocyte maturation, the 3D environment greatly impacts cell behavior and maturation, and so a full understanding of this process requires the use of a more physiologic (3D) environment. Previous studies have shown that growing pluripotent stem cell-derived cardiomyocytes in 3D benefits maturation induction, however, these studies used only single-protein extracellular matrix scaffolds, which do not recapitulate the complexity of the in vivo extracellular matrix. In one embodiment, porcine cardiac extracellular matrix affects cardiomyocyte maturation, however, only modest changes were observed, likely due to the use of a 2D geometry.

In one embodiment, it was found that iPSC-derived cardiomyocytes grown in a complex 3D scaffold behave differently to those in single protein gels (collagen I or fibrin) and that cells in 3D differ considerably from those cultured in 2D. This was especially notable when calcium handling and expression of maturation markers was studied. In one embodiment, biomechanical cues, likely mediated through integrins, were found to be critical.

Fetal and adult cardiac extracellular matrix derived from decellularized heart tissue have a similar composition but differ in their mechanical properties and fiber architecture. The adult extracellular matrix has a higher density of collagen compared to the fetal extracellular matrix, which is similar to what has been shown in rat adult cardiac extracellular matrix. In addition, the stiffness of the adult extracellular matrix hydrogel is 10-fold greater than the fetal hydrogel. These data are in agreement with findings that adult hearts are much stiffer than fetal hearts (10-50 KPa versus 6 KPa), and previous studies have shown that substrate mechanics, particularly stiffness, influence cardiomyocyte growth and maturation. In one embodiment, the induction of maturation genes, such as JCN, by 3D culture and by the presence of adult versus fetal matrix, is largely the result of gel stiffness, which is a consequence of gel composition. In another embodiment, specific matrix proteins engage with specific integrins to mediate maturation signals.

In one embodiment, iPSC-derived cardiomyocytes cultured in 3D cardiac extracellular matrix showed increased expression of calcium handling genes compared to 2D cultures. This result is consistent with previous studies that primarily focused on the expression of ion channels and contractile machinery. In one embodiment, the increase in calcium handling genes supports the result that a 3D geometry significantly influences cardiomyocyte maturation. In vivo, adult cardiomyocytes express higher levels of calcium handling proteins than do fetal cells. This is consistent with the idea that expression of calcium-handling genes can be used as a measure of cardiomyocyte maturity. Interestingly, cardiomyocytes of the adult heart express NCX1 at a lower level than cardiomyocytes of the fetal heart. However, increased NCX1 expression was seen in the 3D cultured cardiomyocytes. In one embodiment, the 3D cardiac extracellular matrix is only one component involved in promoting cardiomyocyte maturation. In one embodiment, additional maturation stimuli (hormones, growth factors, mechanical stretching, signals from non-cardiomyocytes) also affect NCX1 expression. In addition, only a subset of "maturation" genes disclosed here reached elevated levels indicative of maturation when cells were cultured in 3D gels.

Consistent with changes in gene expression, significant differences were found in the calcium-handling in cardiomyocytes, as measured by the calcium flux reporter GCaMP6. Recent publications show that mature cardiomyocytes display increased calcium signaling and kinetics. In one embodiment, in aggregates of iPSC-derived cardiomyocytes, calcium transient amplitude, maximum upslope, and maximum downslope were all increased and the time to 50% decay was correspondingly decreased when cells were in 3D versus 2D. These data are entirely consistent with the findings of increased expression of calcium handing genes/ proteins such as JCN, CASQ2, CaV1.2, and SERCA2a in 3D, which would act to increase the amount of calcium within the sarcoplasmic reticulum (SR) and create cardiomyocytes with a greater capacity to handle calcium during calcium-induced calcium release.

In one embodiment, when cardiomyocytes were seeded as single cells into 3D gels (to allow a more direct comparison of matrix effects in 2D versus 3D), it was found that calcium handling kinetics were different—calcium transient amplitude, maximum upslope, and maximum downslope were all decreased and the time to 50% decay was correspondingly increased when cells were in 3D versus 2D. This illustrates that gene expression is not enough to determine calcium-handling characteristics. Rather, it is the association of cells and the coupling of these calcium-handling systems that determines the kinetics of calcium handling.

In one embodiment, cardiomyocytes were cultured for 7 days before measuring calcium signaling. In another embodiment, cardiomyocytes can be cultured for over 100 days before assaying for maturation. In one embodiment, iPSC-derived cardiomyocytes cultured long term (comparing a 5 month to a 2 month culture) exhibit increased calcium signaling and kinetics suggesting that maturation continues over an extended period of time. Since endogenous cardiomyocytes take several years before maturation is complete, it is not entirely surprising that maturation of cardiomyocyte in culture may take considerable time.

An important characteristic of cardiomyocytes, and one that needs to be recapitulated by iPSC-derived cardiomyocytes, is their response to drugs. In one embodiment, iPSC-derived cardiomyocytes cultured in 3D were found to be more responsive to various stimuli compared to cells cultured in 2D. The addition of the β-adrenergic agonist, isoproterenol, to the iPSC-derived cardiomyocytes cultured in 3D induced an increased beat rate compared to cells in 2D culture. Furthermore, exposure to caffeine induced a steeper slope and a shorter time to maximum calcium concentration in the cardiomyocytes cultured in the 3D cardiac extracellular matrix compared to 2D. In one embodiment, caffeine increases RyR sensitivity by lowering the luminal calcium threshold for calcium release from the SR. In one embodiment, 3D culturing of iPSC-derived cardiomyocytes increases the slope and decreases the time to maximum calcium signaling due to an increase in absolute calcium and/or faster release of calcium from the SR caused by the increased expression of JCN, CASQ2, and triadin, which are all proteins that handle calcium within the SR and modulate its release through the RyR.

In one embodiment, 3D adult cardiac extracellular matrix was used as a strategy to promote iPSC-derived cardiomyocyte maturation. In one embodiment, the age (fetal vs. adult) of the cardiac extracellular matrix modulates its mechanical properties and fiber architecture, and these aspects affect cardiomyocyte gene and protein expression. After 7 days of culture within the 3D adult cardiac extracellular matrix hydrogels, the iPSC-derived cardiomyocytes showed increased expression of many calcium-handling genes, consistent with the increase in these genes seen in adult versus fetal cardiomyocytes. In another embodiment, calcium signaling in the iPSC-derived cardiomyocytes is enhanced in 3D compared to 2D, consistent with the changes in gene expression. The utilization of 3D adult cardiac extracellular matrix to culture pluripotent stem cell-derived cardiomyocytes better recapitulates the in vivo environment than traditional 2D cultures or the use of non-native matrix, thereby promoting cardiomyocyte maturation. In one embodiment, the present disclosure advances strategies for maturing pluripotent stem cell-derived cardiomyocytes, so that they can be safely and effectively used for therapeutic applications to treat heart disease.

There is a critical need to produce adult cardiomyocytes in order to create novel treatments for heart disease. Of the potential sources for these cells, there is growing interest in using iPSCs to generate cardiomyocytes. Unfortunately, iPSC-derived cardiomyocytes are immature and have characteristics of fetal cardiomyocytes, rather than of adult cardiomyocytes. In one embodiment, the present disclosure provides a strategy that utilizes endothelial cells to induce cardiomyocyte maturation. In one embodiment, endothelial cells co-culturing and conditioned medium promote the maturation of iPSC-derived cardiomyocytes. In one embodiment, by using small molecule inhibitors, endothelin-1 protein and notch signaling are, in part, responsible for the increase in cardiomyocyte maturation.

Example 25

Endothelial Cells(EC)

In one embodiment, endothelial cells (EC) affect iPSC-derived cardiomyocyte maturation, and both EC conditioned medium and co-culture promotes cardiomyocyte maturation. This was evident from significantly increased iPSC-derived cardiomyocyte expression of Junctin, SERCA2a, Cx43, CaV1.2, and NCX1 when co-cultured with endothelial cells or in endothelial cell conditioned medium. In vivo the calcium handling proteins, Junctin, SERCA2a, and CaV1.2, are expressed at higher levels in adult cardiomyocytes, compared to fetal cardiomyocytes, thereby supporting the increase in these genes as markers of maturation. Moreover, co-culturing endothelial cells with cardiomyocytes led to an up regulation of miRNAs that resulted in increased expression of Cx43.

The endothelin (ET) family of proteins and peptides consists of four active endothelin isoforms, with ET-1 most prominently expressed within the cardiovascular system. ET-1 is secreted by cardiomyocytes to regulate contraction, hypertrophy and calcium signaling within the heart. ET-1 is known to promote terminal differentiation of developing cardiomyocytes by decreasing proliferation and increasing cell size and binucleation. In one embodiment, ET-1 is responsible, in part, for the increase in maturation by endothelial cells. Downstream, ET-1 is known to enhance NCX1 activity. In one embodiment, this result explains why increased NCX1 expression was observed in CMs grown in EC-conditioned medium and its subsequent reduction in the presence of the ET receptor antagonist PD 142893. While there are two known endothelin receptors (ETA and ETB), ETB is predominantly expressed by endothelial cells in the cardiovascular system while cardiomyocytes express the ETA receptor. In one embodiment, to selectively inhibit ETA, the inventors selected a PD 142893 dose (10 nM) greater than ETA receptor's $IC_{50}$ of 4 nM, but still below ETB receptor's $IC_{50}$ of 15 nM.

In one embodiment, a similar decrease was observed in NCX1 expression following PD 142893 treatment of cardiomyocytes alone, thereby suggesting that iPSC-derived cardiomyocytes secrete and respond to endothelin in an autocrine manner. In addition, the increase in the iPSC-derived cardiomyocyte expression of Junctin, SERCA2a, and Cx43 by endothelial cells conditioned medium was diminished upon incubation with PD 142893 thereby indicating that ET is responsible increased expression of these calcium handling genes. In one embodiment, ET-1 is responsible for the increase in maturation because ET-1 is the predominant isoform within the myocardium.

Notch signaling plays a significant role in the myocardium by regulating cardiomyocyte differentiation and proliferation during development and cardiac remodeling during pathogenesis. Addition of DAPT during endothelial cells/cardiomyocyte co-culture resulted in the decrease in cTNT expression. This is similar to the decrease in cardiac genes in the endothelial cells/cardiomyocyte co-culture with DAPT disclosed in the present application. Notch inhibition, by DAPT, results in the decrease in cardiac maturation genes during endothelial cells/cardiomyocyte co-culture, indicating notch plays a role in iPSC-derived cardiomyocyte maturation.

Endothelial cells play a significant role in promoting the maturation of iPSC-derived cardiomyocyte in vitro. In one embodiment, the present disclosure provides multiple pathways by which may endothelial cells influence cardiomyocyte maturation that include endothelial cells co-culture and secreted factors produced by both endothelial cells and cardiomyocytes. In one embodiment, endothelin, secreted by both endothelial cells and cardiomyocytes, and notch signaling are responsible for the iPSC-derived cardiomyocyte increase in expression of calcium handling genes indicative cardiomyocyte maturation. In one embodiment, the present disclosure illustrates multiple mechanisms of how endothelial cells promote iPSC-derived cardiomyocyte maturation and created a platform that utilizes endothelial cells to generate mature cardiomyocytes that can be used to develop new therapies to treat heart disease.

Example 26

Results

In one embodiment, the present disclosure creates a platform to induce cardiomyocyte (CM) maturation in a similar context that the native CMs would undergo maturation within the developing heart in vivo. The cardiac microenvironment, as disclosed herein comprises cardiac extracellular matrix (ECM) and other non-CM cell types such as endothelial cells and stromal cells.

Figure 12:
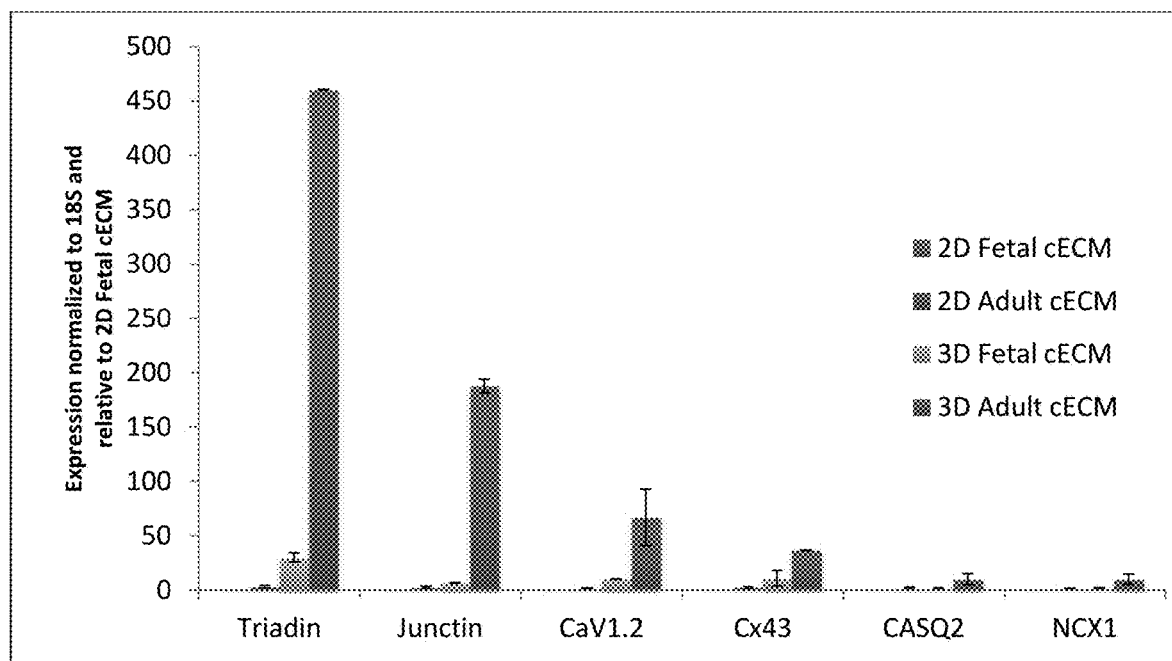
FIG. 12 illustrates, in accordance with embodiments herewith, the three-dimension scaffold and adult cardiac ECM induces highest expression of cardiac maturation genes. The gene expression is measured through quantitative reverse transcriptase polymerase chain reaction and expression is normalized to 18S endogenous control. n=2

Cardiac ECM Promotes CM Maturation:

There are many types of scaffolds that can be used for cardiomyocytes, which include single extracellular matrix protein, synthetic scaffolds, biodegradable scaffolds, hydrogels, etc. Specifically, the present disclosure provides cardiac ECM from fetal and adult bovine heart tissue through SDS-mediated decellularization, and find that in contrast to fetal cardiac ECM, the adult ECM promotes induced pluripotent stem cell-derived CM maturation, as assessed by enhanced expression of mature CM markers (FIG. 12). Even more strikingly, increased levels of maturation was seen when iPSC-derived CM were seeded into a three-dimensional cardiac ECM scaffold compared to growth on 2D surfaces (FIG. 12). In summary, this disclosure demonstrates the use of native cardiac ECM as scaffold that promotes CM maturation. These findings have important implications for studies using iPSC-derived CM to screen for novel drugs, and as therapies for heart disease.

Endothelial Cells Promote CM Maturation:

In one embodiment, endothelial cells were found to play a significant role in inducing CM maturation. There was significant cross talk between the CMs, stromal cells and ECs, which include physical contact and soluble factors. The present disclosure provides multiple modes of action in which EC can induce CM maturation, which include possible roles for Notch and ET-1 signaling. Thus cell types present in the cardiac microenvironment affect CM maturation. Thus, in one embodiment, combining multiple parameters of the cardiac microenvironment, such as the cardiac ECM and vasculature (including endothelial cells and stromal cells) will have beneficial, additive effects on CM maturation.

Cardiac ECM Preparation:

Bovine heart tissue was commercially purchased. The detergents sodium dodecyl sulfate (SDS) and tritonX-100 were used to decellularize the heart tissue. Once all the cells have been removed the scaffold is lyophilized, it was ground into a fine powder and subjected to pepsin digestion in hydrochloric acid. This yields a viscous solution that can polymerize into a three-dimension scaffold when neutralized and brought to 37 degrees C. The cardiac ECM from adult bovine heart was utilized as the three-dimensional scaffold or 2D coating substrate for the cardiomyocytes.

CM Differentiation:

Induced pluripotent stem cells (iPSC) are directly differentiated into CM using small molecules. The iPSC are subjected to GSK3 inhibitor (CHIR99021) and Wnt inhibitor (IWP2) and after 10 days convert into beating clusters of CM. After 21 days of differentiation, the immature CMs are subjected to maturation conditions.

Cardiac Tissues:

The harvested cells ere be embedded into a scaffold that has been neutralized. The cardiac ECM is neutralized with NaOH and diluted to 7 mg/mL. The scaffold was composed of 75% volume of 7 mg/mL of cardiac ECM and 25% volume of 7 mg/mL of fibrinogen. The cells can be seeded at a density ranging from 1-10 million cells/mL within the scaffold. The scaffold polymerization was induced by the addition of thrombin and being place in a 37 degree C. incubator.

Vasculature: Other Cell Types:

Vasculogenesis was utilized to develop in vitro blood vessels in three dimensional scaffolds. The cell types used were endothelial cells and stromal cells. The endothelial cells created the wall of the vessel and sources for these cells types include human umbilical cords, cord blood, pluripotent cells, etc. In addition, the stromal cells that support blood vessel formation and maintenance include cardiac fibroblasts, pericytes, etc.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A cardiomyocyte maturation platform composition, comprising:
   a 3D complex and adult cardiac extracellular matrix (ECM) scaffold and one or more iPSC-derived cardiomyocytes,
   wherein the 3D ECM scaffold is created from the following steps:
   providing a tissue of a subject;
   decellularizing the tissue by incubating it in a solution comprising SDS and subsequent washing with water;
   preparing digested ECM by grating the decellularized tissue to a powder form followed by digestion with pepsin; and
   preparing the 3D ECM scaffold by mixing the digested ECM with fibrinogen.

2. The composition of claim 1, wherein the subject is an adult human.

3. The composition of claim 1, wherein the 3D complex and adult cardiac ECM scaffold is generated from a heart tissue of an adult subject through SDS-mediated decellularization.

4. The composition of claim 1, wherein the 3D complex and adult cardiac ECM scaffold comprises endothelial and/or stromal cells in the 3D complex and adult cardiac ECM scaffold.

5. The composition of claim 1, wherein the one or more iPSC-derived cardiomyocytes may be harvested upon reaching maturity and transplanted into an ischemic heart.

6. The composition of claim 1, wherein the one or more iPSC-derived cardiomyocytes may be harvested upon reaching maturity and used for drug screening.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
attgcattgc tgggcgtctg                                          20

<210> SEQ ID NO 2
<211> LENGTH: 24
<212> TYPE: DNA

```
<213> ORGANISM: Homo sapiens

<400> SEQUENCE: 2
ggcatcatcc acatcaaaat ctcc                                          24

<210> SEQ ID NO 3
<211> LENGTH: 22
<212> TYPE: DNA
<213> ORGANISM: Homo sapiens

<400> SEQUENCE: 3
agcggaccct gaggaaacca tt                                            22

<210> SEQ ID NO 4
<211> LENGTH: 19
<212> TYPE: DNA
<213> ORGANISM: Homo sapiens

<400> SEQUENCE: 4
gggaaggcgg cgaacatct                                                19

<210> SEQ ID NO 5
<211> LENGTH: 22
<212> TYPE: DNA
<213> ORGANISM: Homo sapiens

<400> SEQUENCE: 5
gtccatcgct gccatctacc ac                                            22

<210> SEQ ID NO 6
<211> LENGTH: 22
<212> TYPE: DNA
<213> ORGANISM: Homo sapiens

<400> SEQUENCE: 6
tacagcagca cccccacatt ga                                            22

<210> SEQ ID NO 7
<211> LENGTH: 23
<212> TYPE: DNA
<213> ORGANISM: Homo sapiens

<400> SEQUENCE: 7
tcccctctcg cctatgtctc ctc                                           23

<210> SEQ ID NO 8
<211> LENGTH: 23
<212> TYPE: DNA
<213> ORGANISM: Homo sapiens

<400> SEQUENCE: 8
ctgccccatt cgattttgtt ctg                                           23

<210> SEQ ID NO 9
<211> LENGTH: 24
<212> TYPE: DNA
<213> ORGANISM: Homo sapiens

<400> SEQUENCE: 9
acaagggccc catctacaac tacc                                          24

<210> SEQ ID NO 10
<211> LENGTH: 22
```

```
<212> TYPE: DNA
<213> ORGANISM: Homo sapiens

<400> SEQUENCE: 10
cgatgacgaa gcccacgaag at                                          22

<210> SEQ ID NO 11
<211> LENGTH: 18
<212> TYPE: DNA
<213> ORGANISM: Homo sapiens

<400> SEQUENCE: 11
ccccggccgt ccctctta                                               18

<210> SEQ ID NO 12
<211> LENGTH: 20
<212> TYPE: DNA
<213> ORGANISM: Homo sapiens

<400> SEQUENCE: 12 cgcccctcg atgctcttag                                              20

<210> SEQ ID NO 13
<211> LENGTH: 22
<212> TYPE: DNA
<213> ORGANISM: Homo sapiens

<400> SEQUENCE: 13
agagccccca ggttttgaca ca                                          22

<210> SEQ ID NO 14
<211> LENGTH: 18
<212> TYPE: DNA
<213> ORGANISM: Homo sapiens

<400> SEQUENCE: 14
cgggggattt gggcacag                                               18

<210> SEQ ID NO 15
<211> LENGTH: 24
<212> TYPE: DNA
<213> ORGANISM: Homo sapiens

<400> SEQUENCE: 15
gtggcccagg tccttgaaca taaa                                        24

<210> SEQ ID NO 16
<211> LENGTH: 24
<212> TYPE: DNA
<213> ORGANISM: Homo sapiens

<400> SEQUENCE: 16
gctgcaaact cgccatcaaa ctct                                        24
```